(12) United States Patent
Akiona et al.

(10) Patent No.: US 12,397,430 B2
(45) Date of Patent: Aug. 26, 2025

(54) METHOD AND SYSTEM FOR ELECTROMECHANICAL SAFETY FOR ROBOTIC MANIPULATORS

(71) Applicant: Aescape, Inc., New York, NY (US)

(72) Inventors: Nicholas Akiona, New York, NY (US); Eric A. Litman, Brooklyn, NY (US); David Walsh, Brooklyn, NY (US)

(73) Assignee: Aescape, Inc., New York, NY (US)

( * ) Notice: Subject to any disclaimer, the term of this patent is extended or adjusted under 35 U.S.C. 154(b) by 250 days.

(21) Appl. No.: 17/959,777

(22) Filed: Oct. 4, 2022

(65) Prior Publication Data

US 2024/0109195 A1     Apr. 4, 2024

(51) Int. Cl.
| | | |
|---|---|---|
| *B25J 9/16* | (2006.01) | |
| *B25J 17/00* | (2006.01) | |
| *B25J 19/00* | (2006.01) | |

(52) U.S. Cl.
CPC ........... *B25J 9/1676* (2013.01); *B25J 9/1679* (2013.01); *B25J 17/00* (2013.01); *B25J 19/0004* (2013.01)

(58) Field of Classification Search
CPC ........ B25J 9/1676; B25J 9/1679; B25J 17/00; B25J 19/0004; B25J 9/1674; A61B 34/32; A61B 34/37; A61B 2090/064; A61B 2090/508; A61B 34/30; G05B 2219/40202; G05B 2219/40203
See application file for complete search history.

(56) References Cited

U.S. PATENT DOCUMENTS

| | | |
|---|---|---|
| 6,585,668 B2 | 7/2003 | Nissim |
| D517,218 S | 3/2006 | Kalen |
| D637,304 S | 5/2011 | Feuerabend et al. |
| D637,305 S | 5/2011 | Feuerabend et al. |
| D644,675 S | 9/2011 | Abed |
| D665,093 S | 8/2012 | Sedic |

(Continued)

FOREIGN PATENT DOCUMENTS

| | | |
|---|---|---|
| CN | 203017580 U | 6/2013 |
| CN | 204684116 U | 10/2015 |

(Continued)

OTHER PUBLICATIONS

WO-2023021146-A1 translation (Year: 2023).*

(Continued)

*Primary Examiner* — Kyle T Johnson
(74) *Attorney, Agent, or Firm* — Van Pelt, Yi & James LLP

(57) ABSTRACT

An apparatus includes a base and a robotic arm operatively coupled to the base via a connector. The robotic arm includes a set of links interconnected by a set of joints. A first link from the set of links is operatively coupled to the connector. Each joint from the set of joints includes a brake from a set of brakes, each brake from the set of brakes configured to be enabled or disabled. The apparatus further comprises an end effector operatively coupled to the robotic arm via a second link from the set of links different from the first link. The apparatus further comprises a controller, communicably coupled to at least one of the base, the robotic arm, or the end effector. The controller is configured to cause the robotic arm to perform a task, and determine, during the task, that movement of the robotic arm is to be restricted.

22 Claims, 14 Drawing Sheets

(56) References Cited

U.S. PATENT DOCUMENTS

| | | | |
|---|---|---|---|
| D831,769 S | 10/2018 | Tranchard | |
| D833,028 S | 11/2018 | Olivares et al. | |
| D861,829 S | 10/2019 | Wang | |
| D867,609 S | 11/2019 | Couto et al. | |
| 10,730,189 B2* | 8/2020 | Kuroda | A61B 34/30 |
| 11,285,074 B2 | 3/2022 | Qiu | |
| 11,338,443 B2 | 5/2022 | Eyssautier | |
| 11,865,719 B2* | 1/2024 | Nakamoto | B25J 9/04 |
| 2002/0013641 A1 | 1/2002 | Nourbakhsh et al. | |
| 2005/0166413 A1* | 8/2005 | Crampton | G01B 11/03 33/503 |
| 2007/0000374 A1 | 1/2007 | Clark et al. | |
| 2007/0192910 A1 | 8/2007 | Vu et al. | |
| 2010/0204713 A1* | 8/2010 | Ruiz Morales | B25J 9/041 606/130 |
| 2014/0039517 A1* | 2/2014 | Bowling | A61B 34/74 606/130 |
| 2014/0052153 A1* | 2/2014 | Griffiths | A61B 34/30 606/130 |
| 2015/0119638 A1* | 4/2015 | Yu | A61B 1/0057 600/102 |
| 2015/0257840 A1* | 9/2015 | Mohr | A61B 34/37 606/130 |
| 2015/0351999 A1 | 12/2015 | Brouse | |
| 2016/0157945 A1* | 6/2016 | Madhani | B25J 3/04 606/130 |
| 2017/0172671 A1* | 6/2017 | Miller | B25J 9/1694 |
| 2017/0266077 A1 | 9/2017 | Mackin | |
| 2017/0281254 A1 | 10/2017 | Bonutti | |
| 2017/0334067 A1* | 11/2017 | Swarup | B25J 19/0004 |
| 2018/0296284 A1* | 10/2018 | Miller | B25J 9/1694 |
| 2019/0176334 A1* | 6/2019 | Zhou | A61B 34/37 |
| 2019/0328475 A1* | 10/2019 | Arai | A61B 34/30 |
| 2020/0093555 A1* | 3/2020 | Flatt | A61B 34/30 |
| 2020/0121556 A1 | 4/2020 | Tian et al. | |
| 2020/0281805 A1 | 9/2020 | Qiu et al. | |
| 2021/0085424 A1* | 3/2021 | Hulford | A61B 34/35 |
| 2021/0154852 A1 | 5/2021 | Eyssautier et al. | |
| 2021/0170589 A1* | 6/2021 | Nakamoto | B25J 9/1651 |
| 2022/0088768 A1 | 3/2022 | Kattakuri | |
| 2022/0134551 A1 | 5/2022 | Litman et al. | |
| 2022/0330954 A1* | 10/2022 | Cameron | A61B 34/30 |
| 2022/0387118 A1 | 12/2022 | Litman et al. | |
| 2022/0388165 A1 | 12/2022 | Walsh et al. | |
| 2022/0388168 A1 | 12/2022 | Litman et al. | |
| 2022/0414291 A1 | 12/2022 | Eyssautier | |
| 2023/0165644 A1* | 6/2023 | Deane | A61B 1/0016 700/245 |
| 2023/0404693 A1* | 12/2023 | Hulford | A61B 34/35 |
| 2024/0109195 A1* | 4/2024 | Akiona | B25J 17/00 |

FOREIGN PATENT DOCUMENTS

| | | | | |
|---|---|---|---|---|
| CN | 206416184 U | | 8/2017 | |
| CN | 106068175 B | * | 4/2020 | A61B 34/30 |
| CN | 111053530 A | | 4/2020 | |
| CN | 113908035 A | | 1/2022 | |
| CN | 115870952 | | 3/2023 | |
| CN | 115972202 | | 4/2023 | |
| EP | 3834999 | | 6/2021 | |
| ES | 2910379 T3 | * | 5/2022 | A61B 90/14 |
| SG | 10201809094 A1 | | 5/2020 | |
| WO | WO-2021116554 A1 | | 6/2021 | |
| WO | WO-2021231663 A3 | | 2/2022 | |
| WO | WO-2022056181 A1 | | 3/2022 | |
| WO | WO-2023021146 A1 | * | 2/2023 | A61B 34/30 |

OTHER PUBLICATIONS

CN_106068175_B_I_translation (Year: 2020).*
ES_2910379_T3_I_translation (Year: 2022).*
David, Pradeep, "Cobots—A helping hand to the healthcare industry," Nov. 24, 2017, Universal Robots, 6 pages.
Ex Parte Quayle Action for U.S. Appl. No. 29/732,265, mailed Dec. 2, 2022, 4 pages.
International Search Report and Written Opinion for Application No. PCT/US2021/032111, mailed Jan. 24, 2022, 11 pages.
International Search Report and Written Opinion for Application No. PCT/US2021/049741, mailed Feb. 7, 2022, 5 pages.
Kraus, Rachel, "Bow down before this $310,000 massage mega-robot, human: Who knew the robot uprising would be so good on the shoulders?," Health & Wellness Artificial Intelligence, Dec. 30, 2021, https://mashable.com/article/massage-robot-overlord, 4 pages.
Massage instruments. (Design—© Questel) orbit.com. [Online PDF compilation of references] 17 pgs. Print Dates Range Feb. 24, 2004-Feb. 14, 2020 [Retrieved Nov. 18, 2022] https://www.orbit.com/export/LI CZAH96 B/pdf4/e9bd54bf-4351-4947-8aae-2394fdea7fed-013045.pdf (Year: 2022).
Screen captures from YouTube video clip entitled "Robots can now give full-body personalized massages at home," 11 pages, uploaded Jul. 21, 2020, New Scientist, Retrieved from Internet: https://www.youtube.com/watch?v=t59TXsK1a6c.
Ulanoff, Lance, "Massage Robotics wants you to come and be touched by a robot—if that's your thing," Jan. 6, 2022, Techradar, The source for Tech Buying Advice, 13 pages.

* cited by examiner

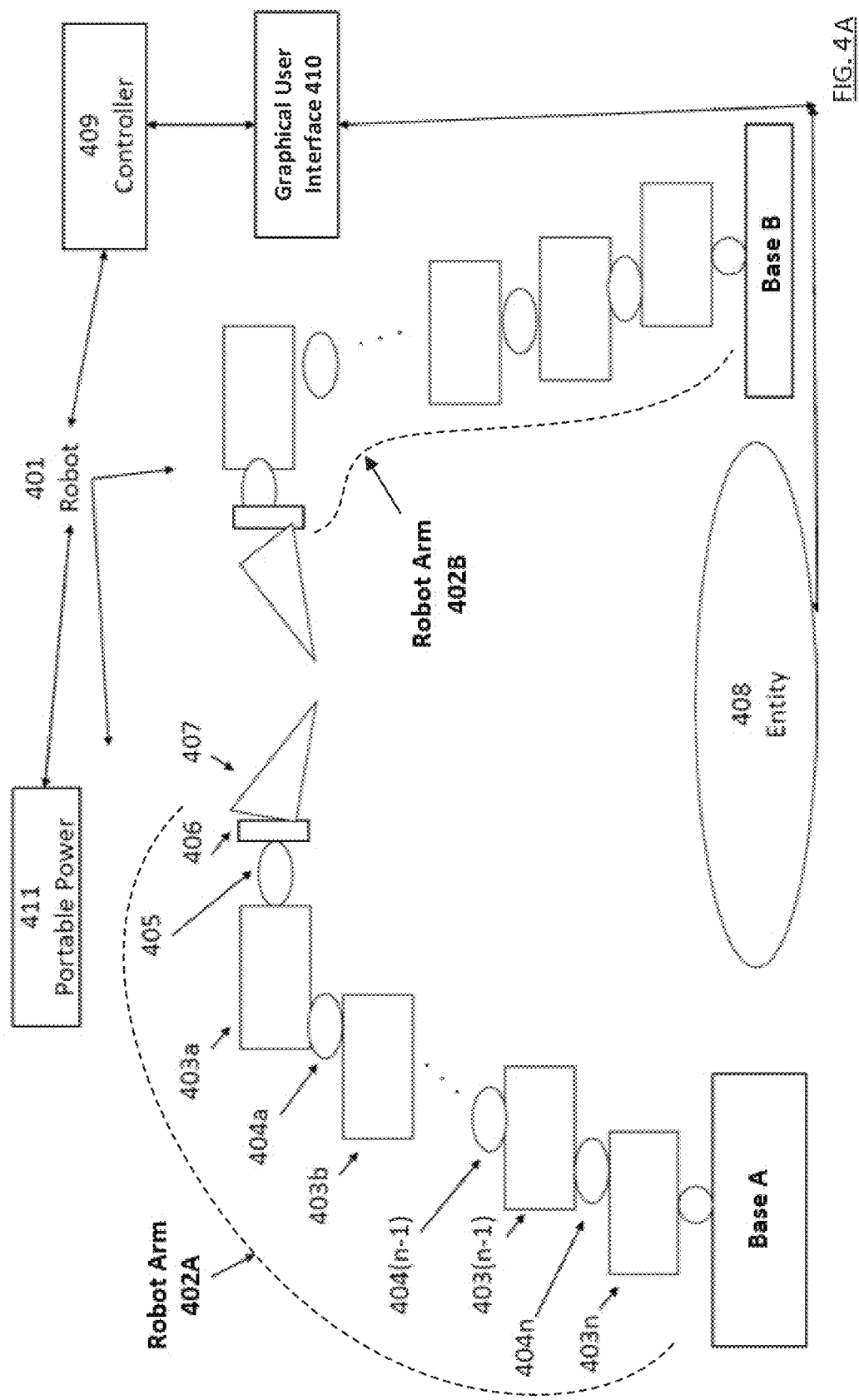

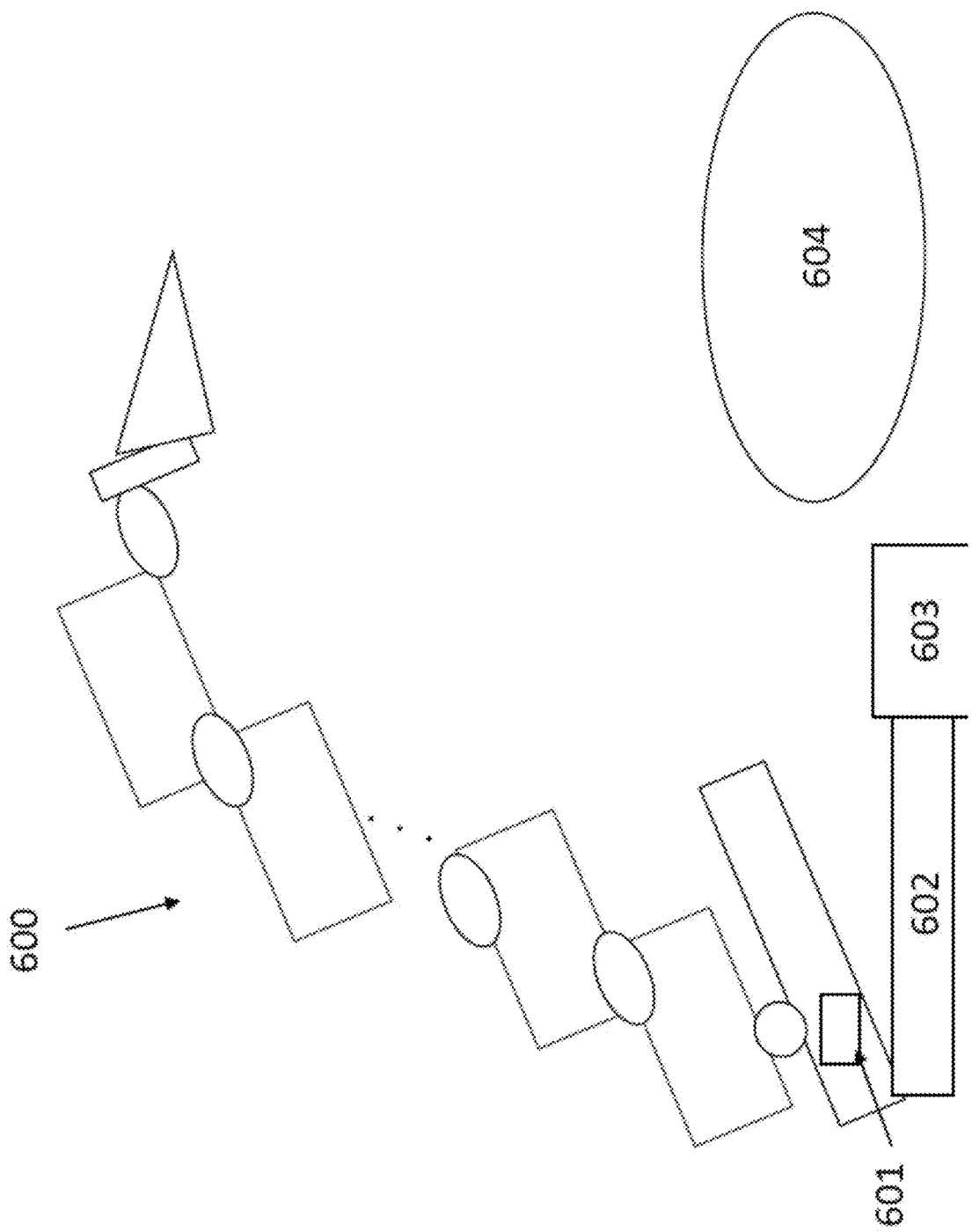

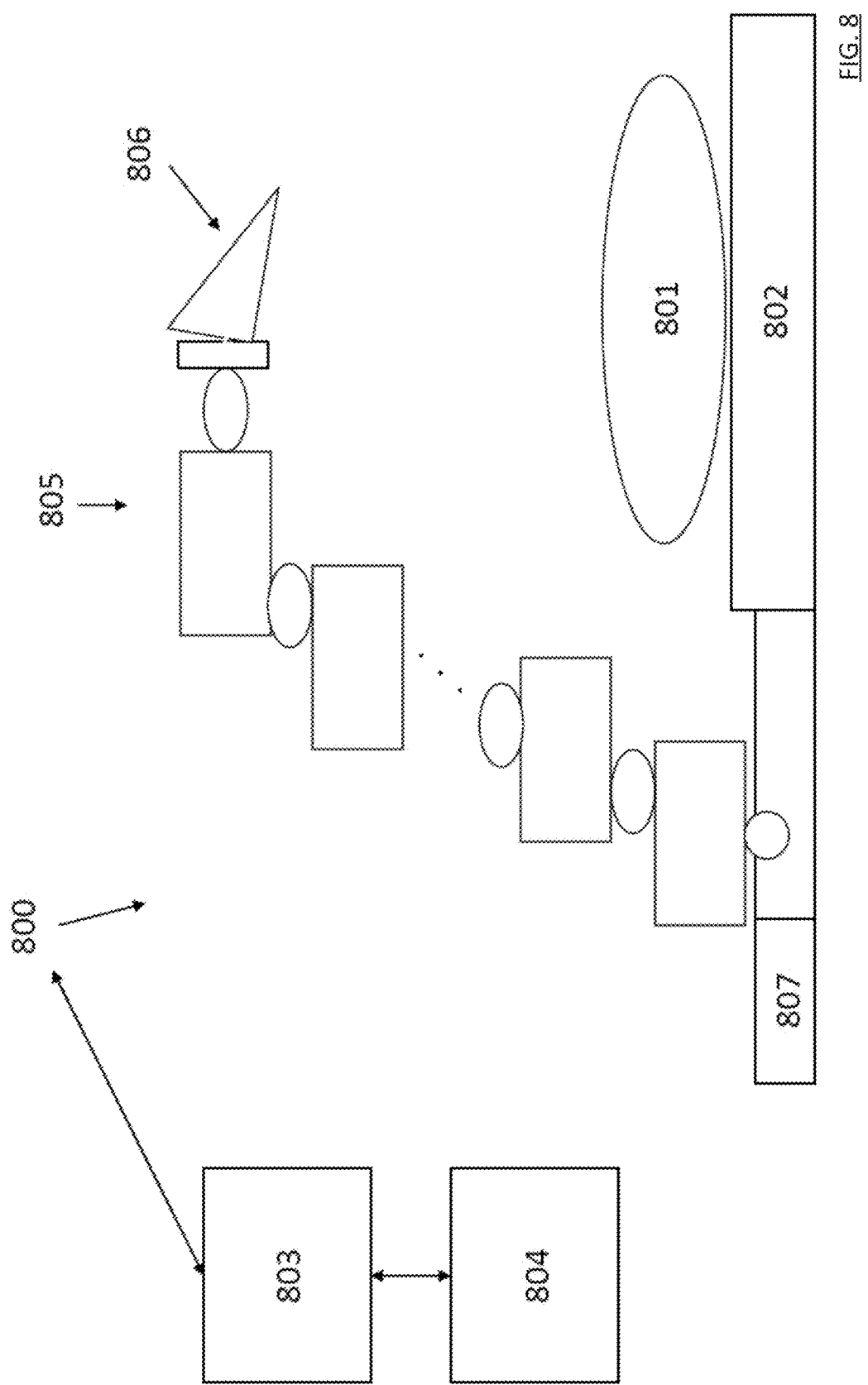

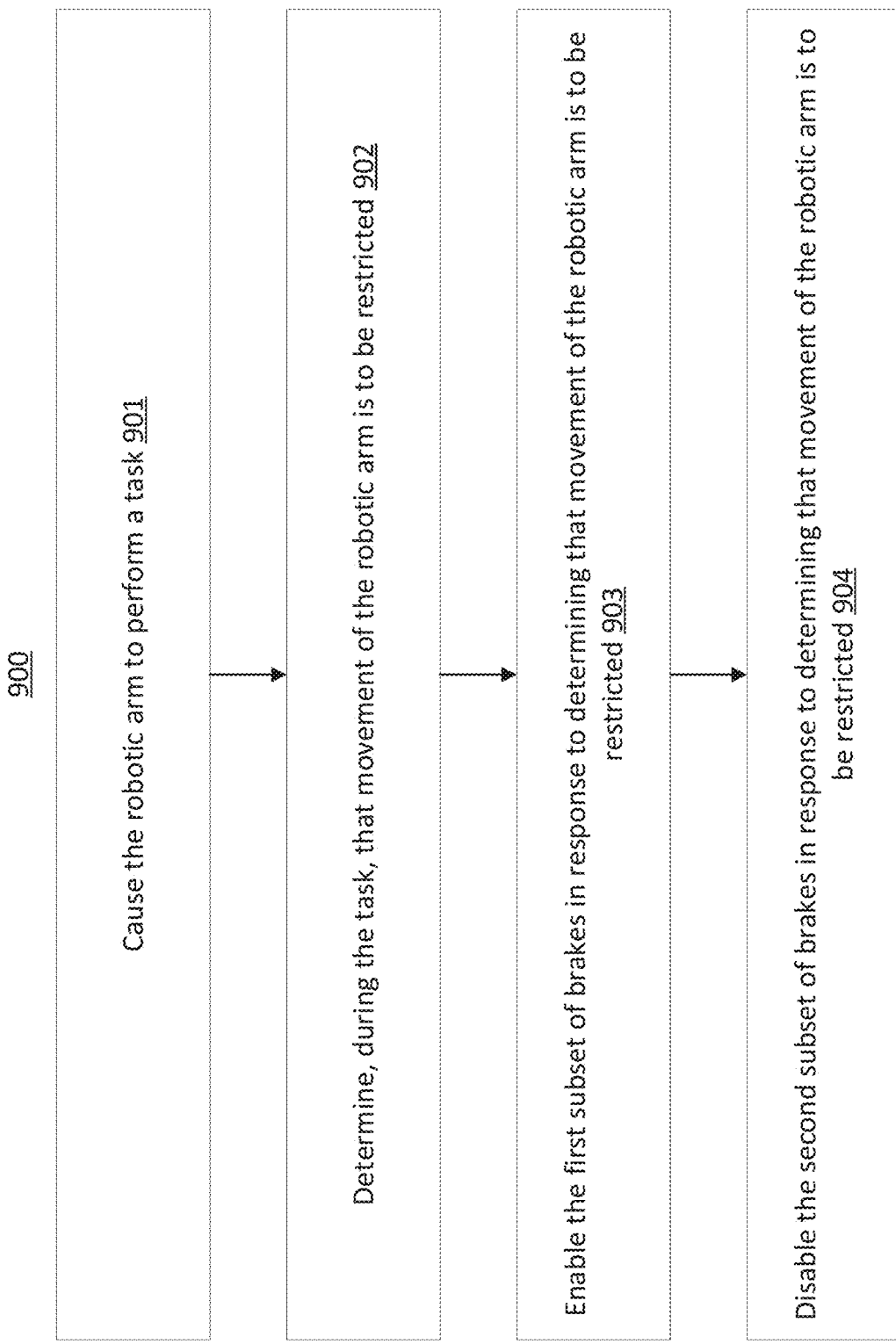

METHOD AND SYSTEM FOR ELECTROMECHANICAL SAFETY FOR ROBOTIC MANIPULATORS

FIELD

The present disclosure relates to systems, methods, and apparatuses for electromechanical safety for robotic manipulators. More specifically, some embodiments of the present disclosure relate to a system, method, and apparatus for electromechanical safety for a robotic manipulator used for applying force to a deformable body.

BACKGROUND

Robotics have been used for various applications, including assembly manufacturing and device testing. For robotics used in manufacturing, various organizations, e.g., Occupational Safety and Health Administration (OSHA), have developed safety guidelines that focus on the "work envelope" (e.g., immediate vicinity or close proximity) of action of the robot, recommending that persons do not enter that work envelope or area of the robot when the robot is powered "on" or active. There are different types of work envelopes identified for robots, including, for example, maximum, restricted, and operating envelopes. These work envelopes can encompass both lateral and vertical areas of movement by the robot. The maximum work envelope space is the maximum area in which the moving parts of the robot can move. The restricted work envelope is a portion of the maximum work envelope which includes restrictions of the device, such as reach limitations, that establish an area not to be exceeded by the robot. The operating work envelope is a portion of the restricted work envelope that is utilized during normal performance by the robot.

A variety of types of accidents exist that can and have happened in use with industrial robots. For example, improper software programming has caused an operator working on the software to be struck by the associated robot. As another example, an operator inappropriately entering the robot's working envelope during operation was pinned by the robot. As another example, an operator accidentally turned on a robot while it was being serviced, causing the robot to strike the maintenance worker. Accordingly, several types of accidents can occur before, during and after use of the robot.

SUMMARY

In an embodiment, an apparatus includes a base and a robotic arm operatively coupled to the base via a connector. The robotic arm includes a set of links (i.e., rigid members or segments) interconnected by a set of joints. A first link from the set of links is operatively coupled to the connector. Each joint from the set of joints includes a brake from a set of brakes. The set of brakes includes a first subset of brakes and a second subset of brakes. Each brake from the set of brakes is configured to be enabled or disabled. The apparatus also includes an end effector (e.g., a tool) that is optionally positioned at an end of a sequence or arrangement of links and joints. The end effector is operatively coupled to the robotic arm via a second link from the set of links different from the first link. The apparatus also includes a controller, communicably coupled to at least one of the base, the robotic arm, or the end effector. The controller is configured to cause the robotic arm to perform a task. The controller is further configured to determine, during the task, that movement of the robotic arm is to be restricted. The controller is further configured to enable the first subset of brakes in response to determining that movement of the robotic arm is to be restricted. The controller is further configured to disable the second subset of brakes in response to determining that movement of the robotic arm is to be restricted.

In an embodiment, an apparatus includes a base and a robotic arm operatively coupled to the base via a connector. The robotic arm includes a set of links interconnected by a set of joints. A first link from the set of links is operatively coupled to the connector. Each joint from the set of joints includes a brake from a set of brakes, each brake from the set of brakes configured to be enabled or disabled. The apparatus also includes an end effector operatively coupled to the robotic arm via a second link from the set of links different from the first link. The apparatus also includes a controller, communicably coupled to at least one of the base, the robotic arm, or the end effector. The controller is configured to cause the robotic arm to perform a task, and to determine, during the task, that movement of the robotic arm is to be restricted.

In an embodiment, a non-transitory, processor-readable medium stores code representing instructions executable by a processor. The code includes code to cause the processor to cause a robot to perform a task that includes causing an end effector included in the robot to contact an object. The robot includes a set of links interconnected by a plurality of joints. Each joint from the plurality of joints includes a brake from a plurality of brakes. Each brake from the plurality of brakes is configured to be enabled or disabled. The plurality of brakes include a first set of brakes and a second set of brakes. The end effector is coupled to at least one of a link from the set of links or an attachment device coupled to the link from the set of links. The code also includes code to cause the processor to determine, during the task, that movement of the robot is to be restricted. The code also includes code to cause the processor to enable the first set of brakes in response to determining that movement of the robot is to be restricted. The code also includes code to cause the processor to disable the second set of brakes in response to determining that movement of the robot is to be restricted.

BRIEF DESCRIPTIONS OF THE DRAWINGS

FIG. 4A shows a diagram of a robot including two robotic arms, according to an embodiment.

FIG. 6A shows a diagram of a robot with an adjustable base, according to an embodiment.

FIG. 8 shows a diagram of a remotely-controllable robot, according to an embodiment.

FIG. 9 shows a flowchart of a method that can be performed by a robot, according to an embodiment.

DETAILED DESCRIPTION

Figure 1:
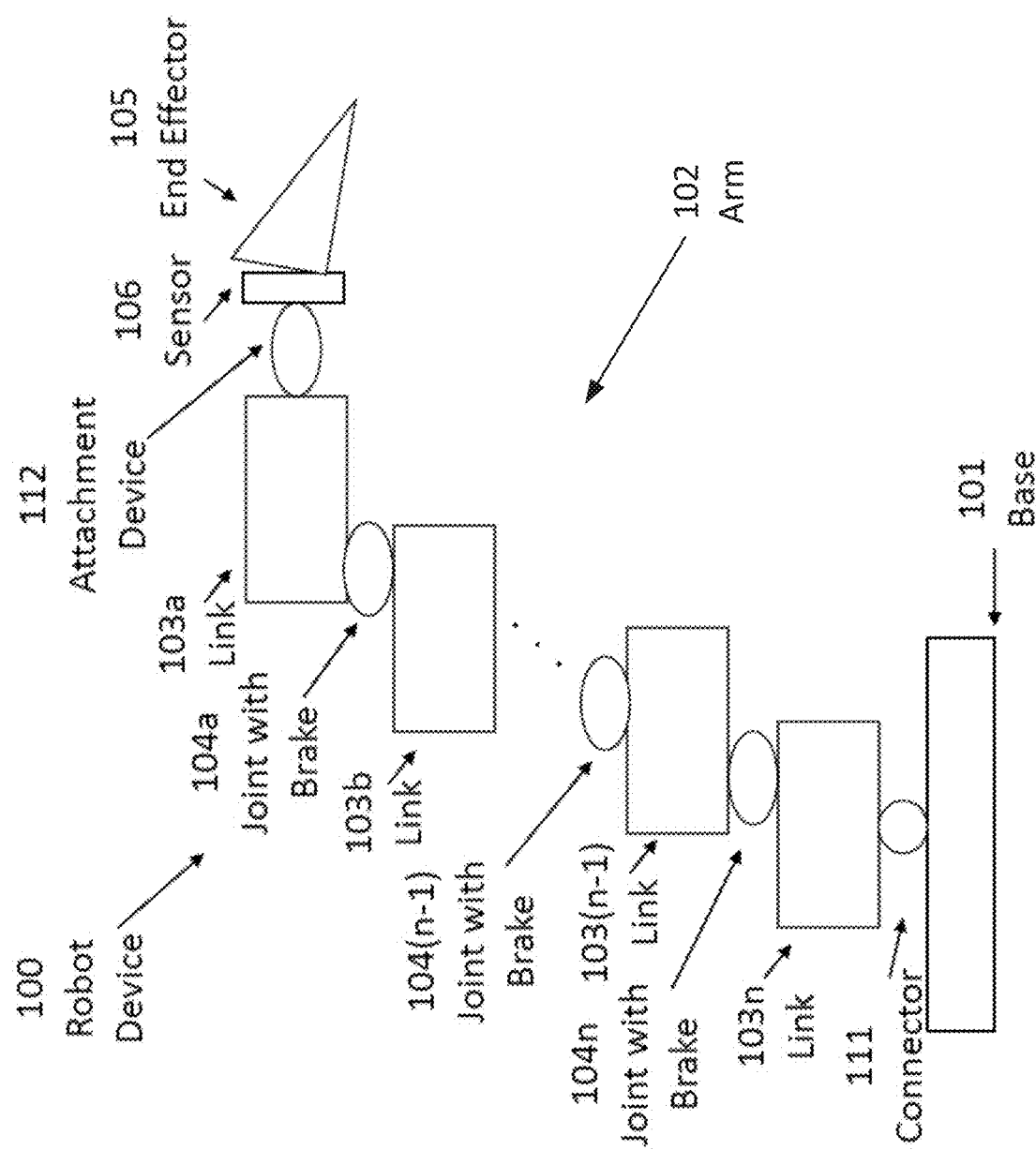
FIG. 1 shows a diagram of a robot with a robotic arm, according to a first embodiment.

The various embodiments described and illustrated herein are for the purpose of showing some example embodiments, and are not intended to limit in any way the scope.

Robots used in industrial work have caused injuries due to a variety of errors. For example, such errors have included human error, control software error, mechanical failure, environmental interference, and unexpected energy surges—all of which could lead to a change in a robot's intended performance. Such potential errors should be accounted for to ensure the safety of those working with or near such robots. Moreover, when the use of robots involves direct contact with a human or other entity, the safety of those being manipulated by the robots should also be accounted for with redundant safety measures.

Gates and/or cages have been recommended for industrial robots, when possible, to prevent persons from accidentally entering the area of action of the robot. However, in the case where a robot is being used by a human operator in close proximity to the robot, or where a robot is in physical contact with a subject entity, e.g., a human, a gate or cage may not always be a viable solution. Similarly, other proposed safety devices such as floor sensors, motion sensors or light curtains designed to stop a robot whenever a person approaches or enters the work envelope of the robot may not always be viable solutions.

The safety implications of a human being worked on by a robot, and/or of a robot operating with an operator in close proximity thereto, are complex and not adequately addressed by known systems. For example, various robot arms available in the marketplace use joint brakes that either unlock when there is a loss of power (which could cause the robot to fall on the subject human/entity and/or operator), or lock when there is a loss of power, causing the robot to become rigid and immovable, and possibly trapping the subject human/entity and/or operator. As mentioned above, floor sensors, and motion sensors, and light curtains do not always provide useful protection when a subject human and/or operator is in close proximity to or contact with a robot. For robots that act on humans more directly or invasively, such as robots used in medical surgery, published OSHA guidelines do not appear to adequately protect the subject human or object that the robot acts upon, and/or the operator of the robot, all of whom are in the work envelope while the robot is active. Accordingly, there exists a need for safety features, in a robot system configured to act upon a person/soft or deformable body/object, that appropriately protect all entities located in the vicinity of the robot system, and that do not unnecessarily cause harm or damage to the robot system during power down or disablement. Moreover, especially in the area of medical or massage applications, improved safety features of a robot system are desirable for better protecting the person/operator controlling and/or working near the robot, and for better protecting the person/entity that the robot is working on during a procedure.

Systems and methods set forth herein address the shortcomings of known robot systems discussed above. More specifically, one or more embodiments of the present disclosure provide for safety features including method, system, and apparatus embodiments, for a robot system acting on an object, such as a human, body, deformable object, and/or the like. The safety features can include a configuration in which a person (e.g., a human being acted on/contacted by a robot) can control the robot remotely, optionally including the ability to remotely power down or disable the robot. Alternatively or in addition, the safety features can include the ability to power down or disable (e.g., remotely and/or automatically) an autonomously working robot acting upon a person/entity. Alternatively or in addition, the safety features can include a configuration in which a person being acted upon by the robot can power down or disable the robot.

One or more method, system, and apparatus embodiments of the present disclosure provide for safety features for a robot system acting in close proximity to a human/body/object (e.g., within 1 inch, within 2 inches, within 6 inches, within 1 foot, within 5 feet, within 10 feet, etc. of the human/body/object).

One or more embodiments of the present disclosure provide for a system in which computer readable instructions are provided, which can be stored on a memory medium, and which can be executed by a controller (e.g., a processor) to disable and/or power down a robot system in a safe manner for any human or body being acted upon at that time.

One or more embodiments of the present disclosure provide for safety features to enhance the safety features currently provided with an "off the shelf" robot from a manufacturer. For example, an "off the shelf" robot may include the capacity for an e-stop or electronic shutdown. If a robot is powered down electronically, however, that may automatically lock the joints of the robot such that the joints cease to move or cannot be moved from a current position. This can effectively trap and/or hurt a human or soft body being operated on by the robot.

One or more embodiments of the present disclosure provide for a robot having at least one robotic arm (or "robot arm"), the robot arm being comprised of an interconnected set of links and powered joints. The robot arm includes manipulators which support or move the wrist of the robot and the end effector. The end effector can be a specialized touch point or other end effector touchpoint designed for attachment to the robot wrist and designed to perform the intended task of making contact with a person or soft body or object.

One or more embodiments of the present disclosure provide for a robot having at least one method for disablement, providing redundancy and improving fault tolerance. The robot arm is configured to act upon an entity such as a person, an animal, a soft body, or an object, whether standing, sitting, or lying down. If lying and/or sitting down, the entity can be disposed on a firm support structure such as a table, chair, or other support structure. The robot actions are controlled by a controller (e.g., a processor), the controller providing electronic instructions to the robot arm to make contact between the touch point and the entity, and to effect one or more actions. The actions can be, among other things, e.g., a massage, a treatment of a specific area of the entity, and/or resistance testing of a specific area of the entity.

One or more embodiments of the present disclosure provide for an electronic shut off of the robot. The electronic shut off can be implemented in a variety of ways such as, for example, as a disabling switch or button on the robot itself, as a separate remote switch (whether wired or wireless (e.g., Bluetooth® enabled)), via a device software application ("app"), and via a command issued by the robot system controller.

One or more embodiments of the present disclosure provide for one or more disabling features of the robot, which can be used in conjunction with or triggered by a shutdown of the robot. Examples of such disabling features can include functionality for disabling certain movements, turning power off, enabling a subset of brakes, disabling a subset of brakes, and/or the like.

One or more embodiments of the present disclosure provide for a disabling feature of the robot in which a mechanical or electro-mechanical brake of one or more of the brakes associated with the joints of the robot arm is removed or otherwise disabled (i.e., not locked/not braked) so that in the event of a shutdown of the robot, the robot arm is not locked in place and instead can be manipulated manually. For example, in the event that a robot is acting upon a person having a massage, and the robot is powered down either intentionally or unintentionally, one or more of the joints of the robot arm are not braked or are not locked. This can allow the person having the massage or a person nearby to manually move the robot arm away from the body to allow the person to leave the treatment area.

One or more embodiments of the present disclosure provide for a disabling feature of the robot in which a mechanical or electro-mechanical brake of the wrist of the robot is removed or disabled such that it cannot be enabled/re-enabled, e.g., automatically and/or in response to a reduction, fluctuation, or loss in power. Similarly, one or more embodiments of the present disclosure provide for a disabling feature of the robot in which a mechanical or electro-mechanical brake of a robot (e.g., t-axis robot) is removed or disabled such that it cannot be enabled/re-enabled. For example, for an n-joint robot arm (where n can be any number, such as 4, 5, 6, 7, 8, 9, 10, etc.), then the (n−1)th and/or nth joint brake (where the joint closest to the base is the $1^{st}$ joint and the joint at the other end of the robot arm closest to the end effector is the nth joint) may be removed/disabled so that it cannot be enabled if the robot loses power or acts on an instruction to stop function, et al. As one example, if there are 6 joints, then the $5^{th}$ and/or $6^{th}$ joint brake may be removed/disabled so that it cannot be enabled. As another example, if there are 7 joints, the $6^{th}$ and/or the $7^{th}$ joint brake is removed so that it cannot be enabled. Of course, other brakes can likewise be removed/disabled, such as the (n−2) brake, (n−3) brake, and/or the like. In some implementations, the mechanical or electro-mechanical brake of the wrist of the robot may be disabled electronically. Alternatively or in addition, the robot may include one or more physical mechanisms (e.g., actuators) that can be adjusted during operation of the robot to prevent or permit the mechanical or electro-mechanical brake of the robot to engage. Alternatively, a mechanical or electro-mechanical brake (e.g., of the wrist or other joint) of the robot may be physically removed from the robot during manufacture of the robot arm.

One or more embodiments of the present disclosure provide for an override of at least one brake associated with a joint of the robot manipulator or arm. In some implementations, an override of the at least one brake is effected by at least one of a safety-rated force sensor, contact sensor, or soft/hard button. In an embodiment, there is an override of the nth and/or (n−1)$^{th}$ brake of a robot arm, using at least one of a safety-rated force sensor, a contact sensor, and/or a soft/hard button.

One or more embodiments of the present disclosure provide for a robot arm or manipulator to be disabled at one or more joint brakes in the event of a dynamic "stop" function by a user, an operator, an operational error, and/or a loss of functionality or power. For example, upon a stop-function of the robot arm or manipulator ("robot"), all of the currently disengaged brakes that were not disabled would engage to lock their respective robot joints. For those joint brakes that were removed prior to this stop-function and/or that received a command from a controller (e.g., a software controller) to disable or not-lock at least one joint brake, a user or operator can then manually move, manipulate and/or push the robot away from an object or body to allow for removal/departure of the object or body. In some implementations, the disabling of one or more joint brakes, but not of all joint brakes, prevents the robot from falling on or otherwise damaging or impairing the object or body or operator using or engaging with the robot. In some implementations, there is a disabling and/or removal of one or more joint brakes of the joints that allow only for lateral movement of the robot in the event of a stop-function, operational error, power loss, or other similar situation. In some implementations, there is a disabling and/or removal of at least one lateral movement joint brake and one upward vertical movement joint brake, to better allow for the manual movement of the robot away from, e.g., a user positioned on a massage table who was previously being massaged by the robot.

In some implementations, by not disabling and/or removing every joint brake, the robot stays intact and does not get damaged unnecessarily (e.g., from falling) in the event of a stop-function, operational error, power loss, or other situation.

One or more embodiments of the present disclosure provide for a robot arm or manipulator to fall back with (e.g., tilt away from) its base attachment in response to an emergency stop condition being triggered, such as a loss of power, a user input, some other safety threshold, and/or the like. One or more embodiments provide for a solenoid located in a portion of the base of the robot or other attachment location, so that when the electric current ceases, the effective magnet behavior of the solenoid ceases, and the portion having the solenoid as an attachment ceases to be attached and lifts up or disengages, allowing the robot arm or manipulator to move away from the entity in a safe manner. One or more embodiments provide for a solenoid at one portion of the robot base attachment to a support or table or standalone base, and for a regular attachment apparatus of a screwed hinge, spring attachment, or other attachment which allows the robot arm or manipulator to angle back or tilt or otherwise relocate away from the entity. One or more embodiments include (A) a solenoid positioned in a base of the robot and/or robot arm, the base being either attached to a supported structure such as a table, or standalone, and (B) an attachment mechanism such as a screwed hinge, spring, etc., involved in facilitating an angling, tilting, or other repositioning of the robot arm/manipulator to move the robot arm/manipulator away from the entity in response to a stop condition. In some implementations, the solenoid can keep the robot stable and engaged during operation, but not after disengaging (e.g., from a stop condition). Although one or more implementations herein are described using a solenoid, other electronically controlled brakes can be used additionally or alternatively. Although the foregoing describes implementations in which a solenoid is part of the robot base attachment to a support or table or standalone base, one or more solenoids can alternatively or additionally be positioned at or in an end effector flange of the robot.

One or more embodiments of the present disclosure provide for a mechanical pressure switch or button that disengages at least one of the brakes associated with one or more of the joints of the robot manipulator or arm. One or more embodiments provide for a mechanical pressure switch or button that disengages at least one brake associated with a last and/or second to last joint or link or wrist joint of the robot. One or more embodiments provide for a mechanical pressure switch or button that disengages at least one brake associated with at least one joint or link or wrist joint of the robot.

FIG. 1 shows an example embodiment of a robot device 100. The robot device 100 has a fixed base 101. The fixed base 101 can be fixed or permanently attached or removably attached to a base structure, support structure, massage table, floor, wall, ceiling, movable carriage, or other structure. The fixed base 101 can be attached to a rail system or block or other structure movably attached to a rail system, allowing the robot device 100 to be moved along the side of a table, chair, wall, floor, or other structure. The robot device has an arm 102 which is pivotably connected, via connector 111, to the fixed base 101. The arm 102 includes one or more segments or links 103a . . . 103n (where n can be any number, such as 2, 3, 4, 5, 6, 7, 8, 9, 10, etc.). Each of the links 103a . . . 103n are connected (e.g., interconnected) to each other at a joint portion 104a . . . 104n. At an end of the link 103a, an end effector or touch point 105 can be removably attached (e.g., via a device 112). The device 112 can be a joint, screw, magnet, hinge, adhesive, or other available attachment device. In an embodiment, at least one of a sensor, a force sensor or a detection device 106 is located at, on, or near at least one of the device 112, the end effector 105, or the link 103a. In an embodiment, the end effector 105 is attached directly to the link 103a (e.g., without device 112 and/or sensor 106). In an embodiment, the sensor 106 detects a force being exhibited by the robot device 100 on an entity (not shown in FIG. 1) that exceeds a threshold level and signals an immediate electronic shutdown of the robot device (e.g., automatically and without requiring human intervention). The threshold level can be stored in a memory (not shown in FIG. 1) (e.g., a local database, remote database) or other location that is accessible by a controller (not shown in FIG. 1) which operates the robot device 100 and/or gives instructions or commands to the robot device 100.

The controller (not shown in FIG. 1) can be, for example, a hardware based integrated circuit (IC) or any other suitable processing device configured to run and/or execute a set of instructions or code. For example, the controller can be a general-purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. In some implementations, the controller can be configured to run any of the methods and/or portions of methods discussed herein. The controller can be housed at any one or more components of the robot device 100, or somewhere different than the robot device 100. Signals sent by the controller can be communicated to one or more components of the robotic device 100 (e.g., via a system bus), such as base 101, connector 111, joint portion 104a . . . 104n, links 103a . . . 103n, device 112, sensor 106, end effector 105, and/or a combination thereof. In some implementations, the controller continuously sends a signal (e.g., a power or command signal) and/or keeps a pin tied 'high' to prevent the brakes from engaging. The removal of the signal, in turn, can cause the brakes to engage.

The memory (not shown in FIG. 1) can be, for example, a random-access memory (RAM), a memory buffer, a hard drive, a read-only memory (ROM), an erasable programmable read-only memory (EPROM), and/or the like. The memory can be configured to store data used by the controller to perform the techniques discussed herein. In some instances, the memory can store, for example, one or more software programs and/or code that can include instructions to cause the controller to perform one or more processes, functions, and/or the like. In some embodiments, the memory can include extendible storage units that can be added and used incrementally. In some implementations, the memory can be a portable memory (for example, a flash drive, a portable hard disk, and/or the like) that can be operatively coupled to the controller. In some instances, the memory can be remotely operatively coupled with the robot device 100. For example, a remote database device (not shown in FIG. 1) can serve as a memory and be operatively coupled to the robot device 100. The memory is operatively coupled to the controller.

In an embodiment, the sensor 106 (e.g., a force sensor and/or a detection device) measures the force or other measurable matter by the end effector or touch point 105 in contact with an entity, and compares that measurement to a predetermined threshold level. If the measurement exceeds the threshold level, a remedial action can be triggered, such as effecting an alarm/buzzer or other light or sound notification. If the measurement exceeds the threshold level, this can trigger a command by the controller to lock, partially lock, stop, and/or move (e.g., to a predefined position), depending upon the preset controller command. The controller can optionally also trigger an electronic shutdown of the robot device 100.

In an embodiment, a user or operator can push a button (not shown in FIG. 1; or any other similar component) that immediately initiates a stop-function of the robot device 100 (e.g., arm 102). The button can be located anywhere on the robotic device 100, such as at/on the fixed base 101, the connector 111, joint portion(s) 104a . . . 104n, link(s) 103a . . . 103n, attachment device 112, sensor 106, end effector 105, and/or a combination thereof. Additionally or alternatively, the button can be located remote from the robotic device 100, but have wireless and/or wired communication capability with the robot device 100.

The end effector 105 can be any type of end effector 105, such as a gripper, a roller, a suction cup, a powered tool, a massage tool, and/or the like. In some implementations, the end effector is shaped for performing a massage technique, such as pinning, rolling, stretching, grabbing, and/or the like.

Figure 2:
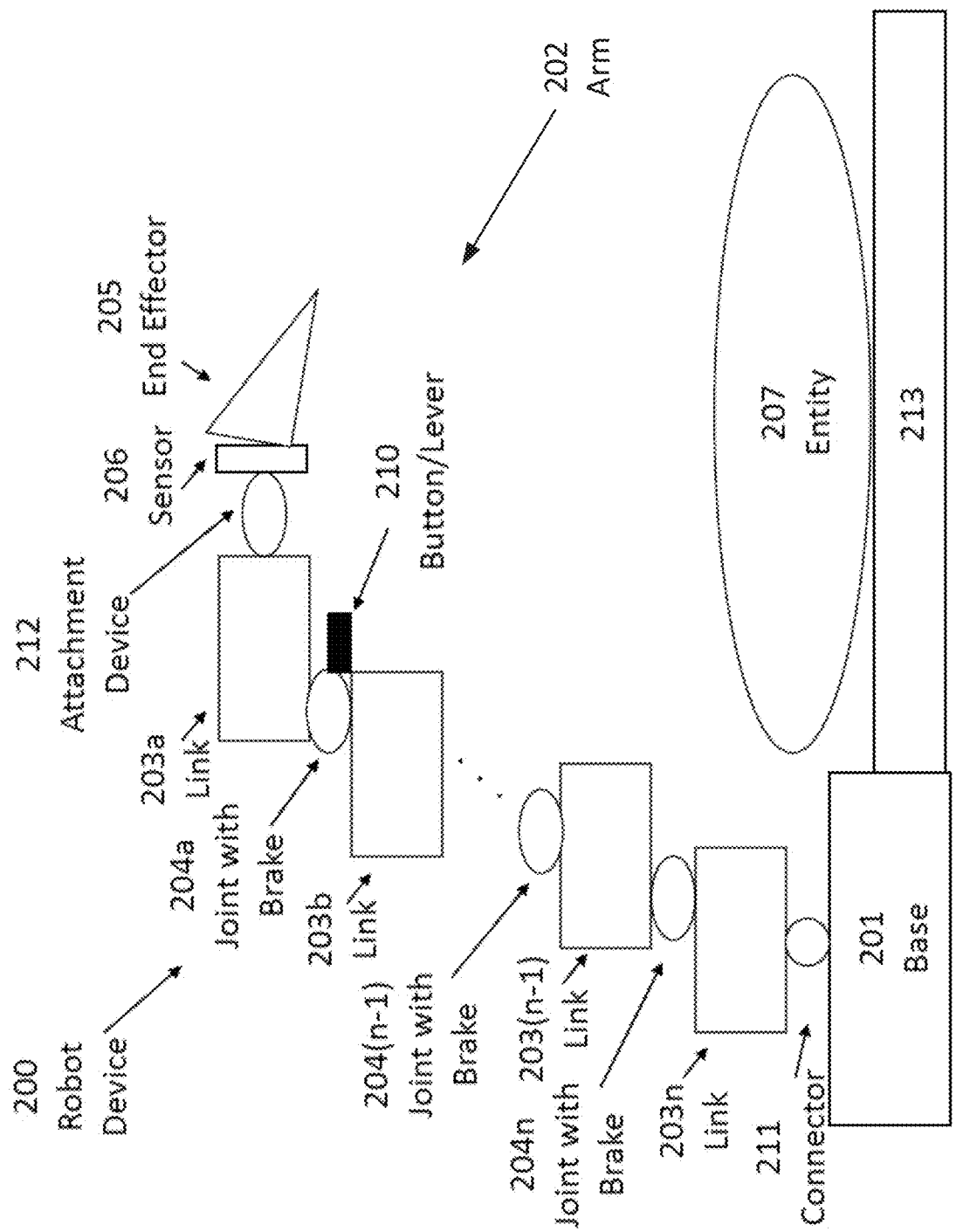
FIG. 2 shows a diagram of a robot with a robotic arm, according to a second embodiment.

FIG. 2 shows an example embodiment of a robot device 200 acting upon an entity 207 such as an object, soft body, or human/animal body. Similar to robot device 100, robot device 200 can include a memory and a controller operatively coupled to the memory. The robot device 200 has a fixed base 201. In an embodiment, the fixed base 201 can be fixed or permanently attached or removably attached to a base structure 213 such as a support structure, massage table, floor, wall, ceiling, movable carriage, or other structure. In an embodiment, the fixed base 201 can be attached to a rail system or block or other structure movably attached to a rail system, allowing the robot device to be moved along the side of a table, chair, wall, floor, ceiling, housing, or other structure. The robot device 200 has an arm 202 which is at least one of connected, movably connection and pivotably connected, via connector 211, to the fixed base 201. The arm 202 includes one or more segments or links 203a ... 203n (where n can be any number, such as 2, 3, 4, 5, 6, 7, 8, 9, 10, etc.). Each of the links 203a ... 203n are connected to each other at a joint portion or joint portions with brake 204a ... 204n. In an embodiment, at least one of joint portion 204(n−1) and 204n, the brake can be removed (e.g., mechanically removed) prior to use of the robot device 200. This can allow that, when a stop-function, malfunction, or loss of power occurs, an operator or user can move at least one or more portions of the robot arm 202 so that a user is not trapped by the robot arm 202.

In an embodiment, an end effector or touch point 205 can be removably attached via a device 212 at the end of the robot arm 202 and at link 203a. The device 212 can be a joint, screw, magnet, hinge, adhesive, welding, or other available attachment device or method. In an embodiment, a force sensor or detection device 206 is located at, on, or near at least one of the attachment device 212, the end effector 205, or the link 203a. In an embodiment, the end effector 205 is attached directly to the link 203a (e.g., without device 212 and/or sensor 206). In an embodiment, the sensor 206 detects, e.g., a force being exhibited by the robot device 200 on an entity 207 that exceeds a threshold level and signals an immediate electronic shutdown of the robot device (e.g., automatically and without requiring human intervention). In an embodiment, the sensor 206 is an electromechanical sensor that triggers an electronic signal that shuts down the robot arm 200 in connection with the electromechanical sensor 206, upon sensing a specific force or improper direction of the end effector 205. In an embodiment, the sensor 206 is an electromechanical sensor 206 that is associated with a standalone controller and memory storage that compares the sensed data (e.g., force data) with at least one preset threshold, and effects at least one of a shutdown of the robot arm 202 and one or more robot arm joint brakes. Sensor 206 can be any type of sensor. In some implementations, arm 202 does not have to be an "arm," but can have a different shape. The use of a robot arm in the embodiments described herein is meant for explanatory purposes and not intended to limit the scope of the invention.

In an embodiment, the entity 207 (or someone else different than the entity 207) can push a button or lever 210 that initiates immediately at least one of the at least one joint portion 204a ... 204n to move at least one or more of the arm links 203a ... 203n up or in a direction away from the entity 207. The button or lever 210 can be located at one or more of the joints to disable a brake of the joint.

Figure 3:
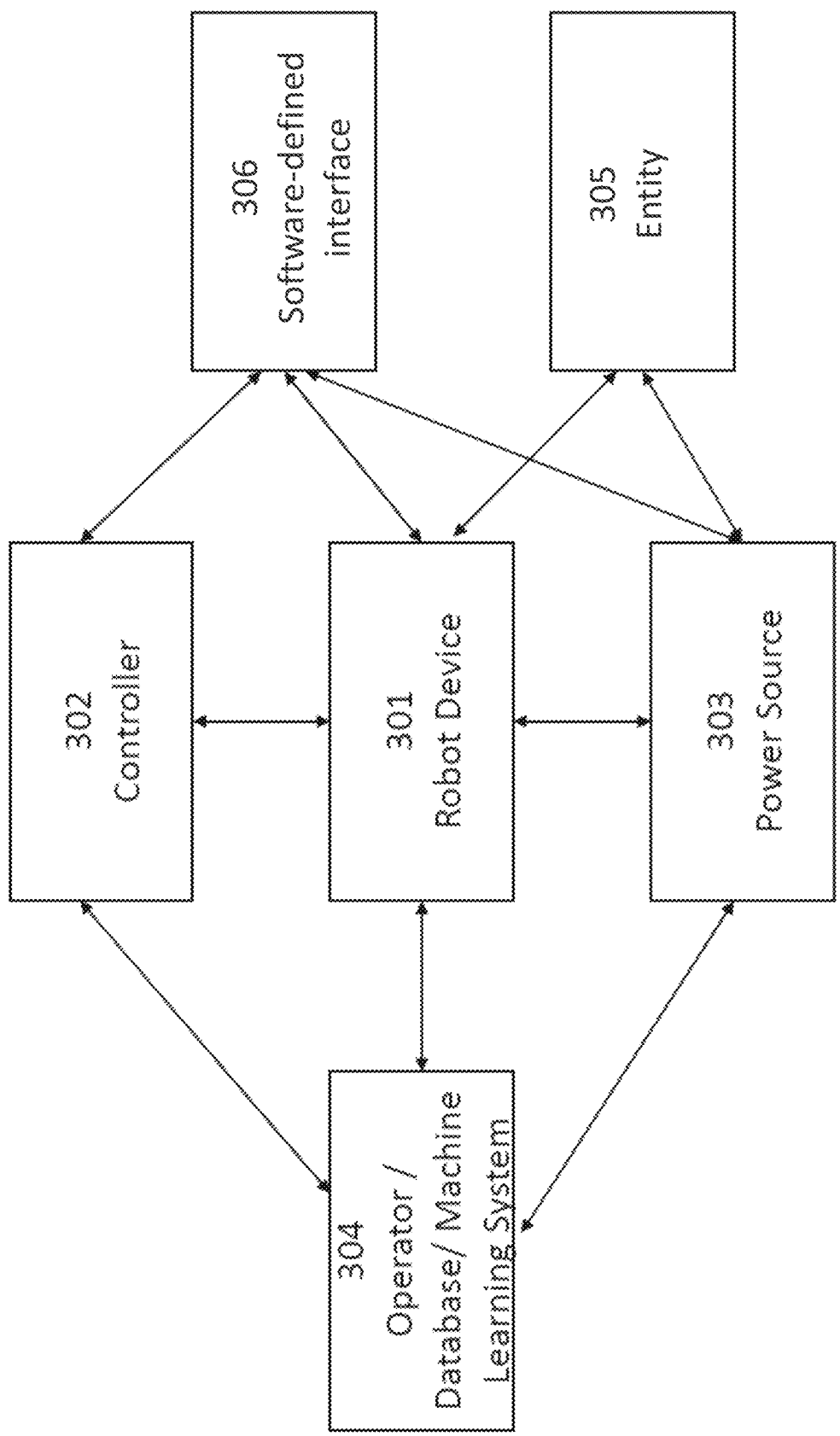
FIG. 3 shows a block diagram associated with a robot, according to an embodiment.

In FIG. 3, a robot system embodiment is shown having a robot 301 which is situated in order to act upon an entity 305, such as an object, soft body, or human. The robot 301 is comprised of a set of links that are interconnected by a set of powered joints, such as those shown in the embodiments of FIGS. 1 and/or 2. The robot 301 is powered by a power source 303 using AC or DC current, which may be, for example, a portable battery or otherwise. The robot 301 and the controller 302 communicate via direct connection, LAN, WLAN, Bluetooth, or other available connection. The controller 302 provides computer software commands to the robot 301 in order effect an action by the robot 301. The controller 302 can be a processor, computer, or a networked computer software system, or other available device. An additional entity 304—such as an operator or a database of instructions and commands, or a machine learning computer software system—can be present to give commands and/or control the controller 302. The entity 305 being acted upon by the robot 301 can have access to a software-defined interface (e.g., processor tablet, remote control, mobile device, or other computer software device) 306 capable of giving commands and/or requests to the controller 302, robot device 301, and/or power source 303. The entity 305 being acted upon by the robot device 301 can have access directly to the robot 301 and/or power source 303. This access by the entity 305 or software-defined interface 306 can allow, for example, for the entity 305 to stop the robot 301 in the event of malfunction and/or manipulate the robot 301 in the event of unexpected power loss or event.

A system embodiment of a robot 401 having two robot arms (402A, 402B) is shown in FIG. 4A, with the robot arm 402A including a base "A," an interconnected set of links 403a ... n and powered joints 404a ... n. The robot arm 402A includes a manipulator 405 that supports or moves a wrist 406 of the robot arm 402A and an end effector 407. The end effector 407 can be a specialized touch point or other end effector device designed for attachment to the robot wrist 406 and designed to perform an intended task that may include making physical contact with an entity 408. In some implementations, the entity 408 includes at least one of a human person or other soft body or object 408. In some implementations, the robot 401 is electronically controlled by a controller 409 that sends commands to one or more electronic components of the robot 401, e.g., to at least one actuator, in order to effect the commands. The controller 409 can be directly controlled by the entity 408 via a compute device (e.g., via a graphical user interface (GUI) 410 displayed at the compute device and/or via a software application or "app" running on the compute device) and/or can be controlled automatically by at least one of a processor, a programmable logic controller (PLC), a computer system, a networked computer system, or a machine learning computer software program/system (e.g., according to pre-programmed routines, rules, or other code), or can be controlled via a hybrid automatic-manual system. Robot arm 402B includes a base "B," and can include some or all of the structure and/or functionality of robot arm 402A as described herein.

In some implementations, when the robot 401 does not execute a command properly, or another malfunction occurs, the robot 401 (e.g., via the controller 409) shuts down the robot, disables at least one feature of the robot 401, enables at least one feature of the robot 401, and/or modifies at least one feature of the robot 401. For example, in some implementations, when the robot 401 is disabled, the robot arm joints 404a ... n connecting the different links 403a ... n of the robot arm 402A are not powered. When this occurs, the robot arm joints do not allow movement, and are locked in place. Each of these joints are locked using a joint brake which can be electronic, electromechanical or mechanical. It can happen that when the robot arm 402A locks in place, the entity 408 may be trapped and/or enclosed by the robot arm 402A or trapped against or near a structure by the robot arm 402A. This can be a dangerous situation, for example, if a person getting a massage is trapped on a massage table by the robot arm. In this example, the person may be lying face down, and unable to escape or even see what is occurring. Further, the person may be unable to dislodge a mechanical brake(s) of one or more joints of the robot arm 402A. Accordingly, in this situation, an embodiment of a localized or portable power source 411 associated, attached, or in some way able to give limited power to the robot arm 402A is possible, allowing for the system to effect an automatic withdrawal of the robot arm 402A from the area of the entity 408. This allows the entity 408 to depart safely.

In some embodiments, the robot 401 is configured to automatically reposition one or more components thereof (e.g., the base "A," the robot arm 402A (or any component or grouping of components thereof), the base "B," and/or the robot arm 402B (or any component or grouping of components thereof)), to remove or reduce a force applied to the entity 408, for example in response to a loss of power, a power fluctuation, a reduction in power, or a detected abrupt movement meeting predefined criteria. The automatic repositioning can include one or more of: translating the one or more components along a direction extending away from the entity 408, rotating the one or more components away from the entity 408, reducing a force applied to the entity 408 by the one or more components, removing a force applied to the entity 408 by the one or more components, or causing the end effector to cease making contact with the entity 408. The automatic repositioning can include locking of one or more brakes associated with the one or more components, where the default during operation is an unlocked condition. Similarly, the repositioning can include unlocking of one or more brakes associated with the one or more components, where the default during operation is a locked condition (e.g., base "A" and/or base "B").

In some embodiments, at least one of the robot arm 402A (i.e., any component(s)/joint(s) thereof) or the robot arm 402B (i.e., any component(s)/joint(s) thereof) includes a reconfigurable ratchet to selectively limit a first direction of movement thereof, and to facilitate incremental movement thereof in a second direction opposite the first direction. The ratchet can be a mechanical device that permits continuous or discontinuous (e.g., stepped) linear or rotational movement along only a first direction while preventing movement along a second direction opposite the first direction. The ratchet optionally includes a mechanical switch that is switchable between/among two or more positions, for example such that when the mechanical switch is in a first position, the ratchet permits movement in the first direction but not in the second direction, and when the mechanical switch is in a second position, the ratchet permits movement in the second direction but not in the first direction. In some implementations, the ratchet is configured to lock (i.e., to prevent movement in) in each of a first direction and a second direction. The ratchet can include a plurality of teeth configured to engage/mate with complementary-shaped cogs, teeth, or "pawls." In some implementations, the default condition of the ratchet during operation of the robot arm 402A/402B is an unlocked condition, and the cogs, teeth, or pawls may be spring-loaded or otherwise mechanically retained in the unlocked position until engagement of the ratchet is triggered. In some implementations, movement of the robot arm 402A and/or robot arm 402B includes a mechanical and/or electronic limiter to prevent the robot 401 from tipping over or otherwise becoming imbalanced, while the ratchet is being used.

Figure 4C:
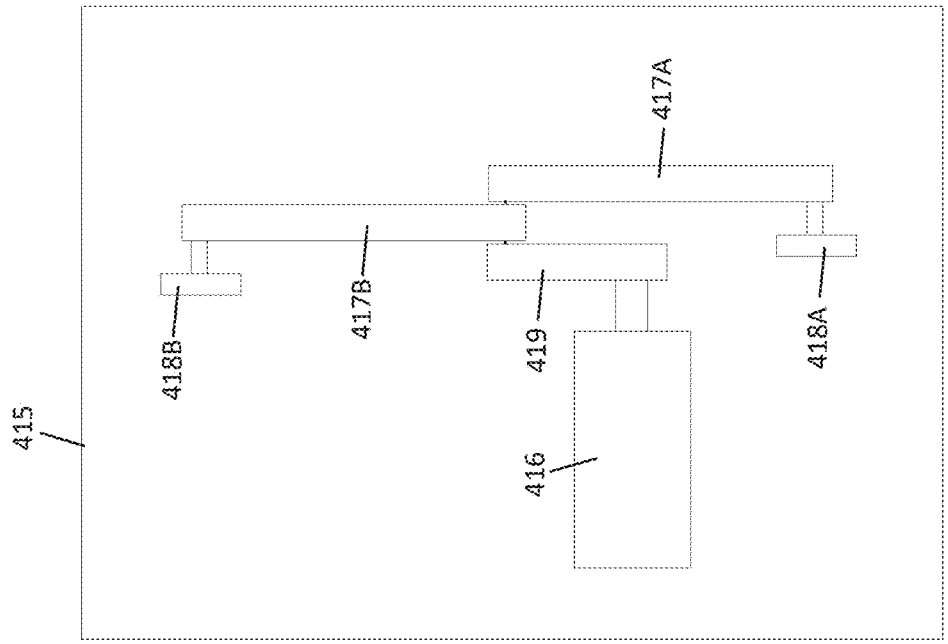
FIG. 4C shows a side view of the joint from FIG. 4B, according to an embodiment.
Figure 4B:
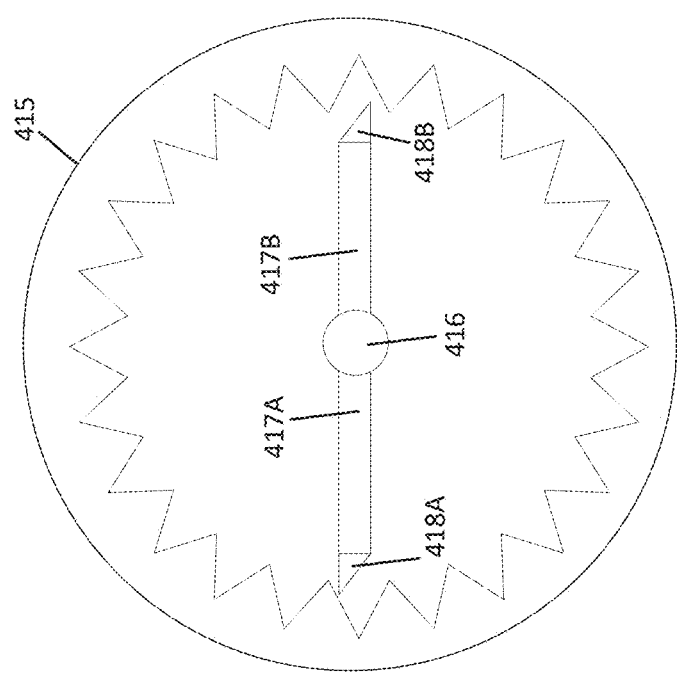
FIG. 4B shows a section view of a joint with ratcheting functionality, according to an embodiment.
Figure 4E:
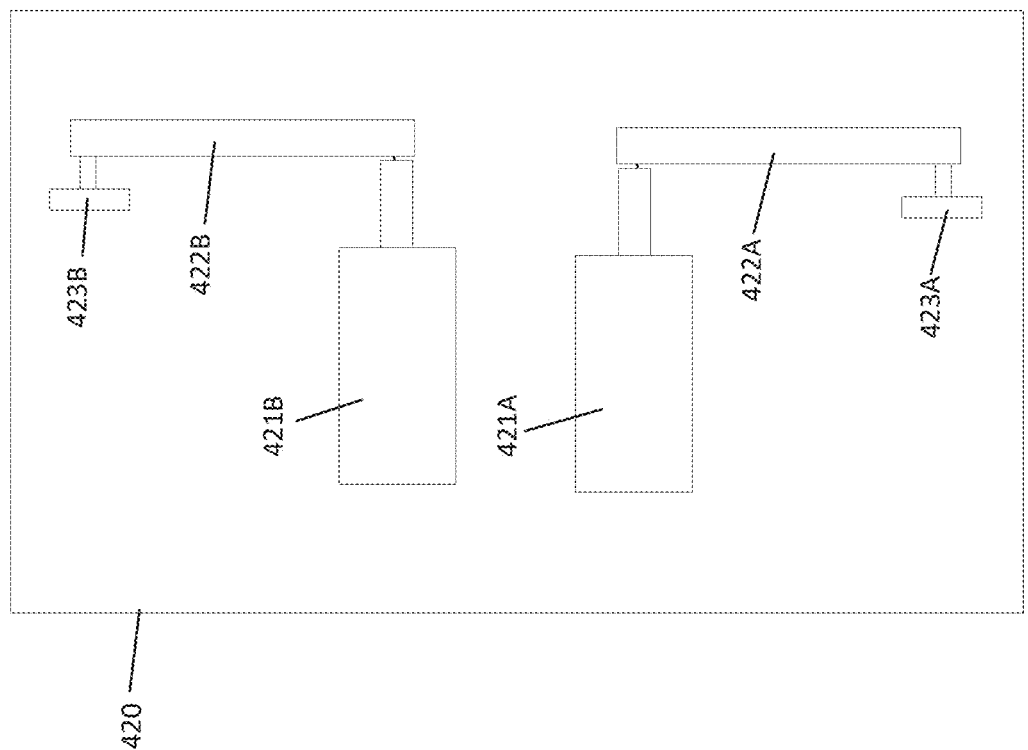
FIG. 4E shows a side view of the joint from FIG. 4D, according to an embodiment.

FIG. 4B shows a section view of a joint 415 that can perform a ratcheting function, according to an embodiment. As the motor 416 rotates, pawls 418A, 418B can each extend and/or retract (e.g., via a solenoid included in pawls 418A, 418B). For example, FIG. 4B shows a first configuration, where both pawls 418A, 418B are extended such that the joint 415 will not rotate substantially (e.g., will not rotate greater than a distance of one tooth spacing). In some implementations, the motor 416 can rotate such that, via links 417A, 417B and crank 419 (shown in FIG. 4C; not shown in FIG. 4B), both pawls 418A, 418B are retracted and joint 415 can rotate substantially freely in a clockwise and/or counterclockwise direction. In some implementations, the motor 416 can rotate such that pawl 418A is extended and pawl 418B is retracted so that the joint can rotate substantially in a first direction (e.g., clockwise), but not a second direction (e.g., counterclockwise). In some implementations, the motor 416 can rotate such that pawl 418A is retracted and pawl 418B is extended so that the joint cannot rotate substantially in the first direction (e.g., clockwise), but can rotate in the second direction (e.g., counterclockwise). In some implementations, the pawls 418A, 418B each include a solenoid that can extend or retract, thereby configuring the joint 415 to rotate substantially in the first direction but not the second direction, the second direction but not the first direction, both the first direction and the second direction, or neither the first direction nor the second direction. FIG. 4C shows a side view of the joint 415 from FIG. 4B, according to an embodiment. As the motor 416 rotates, via the crank 419 and links 417A, 417B, the pawls 418A, 418B can extend and/or retract.

Figure 4D:
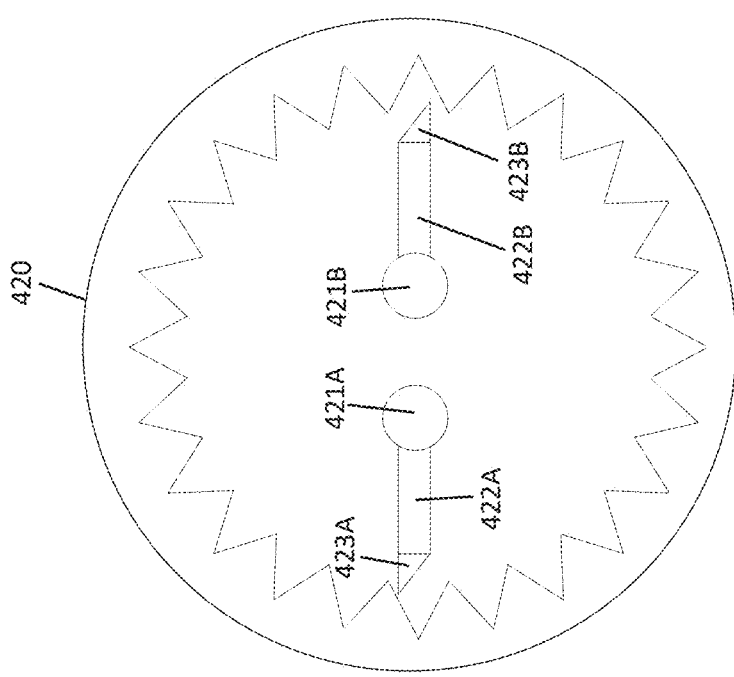
FIG. 4D shows a section view of a joint with ratcheting functionality, according to an embodiment.

FIG. 4D shows a section view of a joint 420 that can perform a ratcheting functionality, according to an embodiment. Compared to joint 415 from FIG. 4B, joint 420 includes two motors 421A, 421B. Pawl 423A can extend or retract via link 422A as motor 421A rotates, while pawl 423B can extend or retract via link 422B as motor 421B rotates. Through combinations of pawls 423A, 423B being extended or retracted, the joint 420 can be configured to rotate substantially in a first direction (e.g., clockwise) but not a second direction (e.g., counterclockwise), the second direction but not the first direction, both the first direction and the second direction, or neither the first direction nor the second direction. FIG. 4D shows a side view of a joint 420, according to an embodiment. As motor 421A rotates, pawl 423A can extend and/or retract via link 422A, while as motor 421B rotates, pawl 423B can extend and/or retract via link 422B.

Although each of joints 415, 420 is shown as including two pawls, in other implementations, more than two pawls can be used (e.g., for redundancy and/or additional functionality). Although the motors, pawl, links, cranks, and/or rotating gears of joints 415, 420 are shown as being located interior to joints 415, 420, in some implementations, the motors, pawls, links, cranks, and/or rotating gears can be located exterior to joints 415, 420.

In some embodiments, an additional joint is positioned at the base of the robot arm 402A and/or 402B and the base and/or the additional joint can be actuated or repositioned using a solenoid and/or a latch mechanism. In some such implementations, the actuation/repositioning of the additional joint is accomplished purely mechanically (i.e., not via software). For example, the additional joint can be configured for mechanical actuation using one or more of: spring-loading, gravity-based movement, rotational force (e.g., a spinning gear or motor), a locking mechanism (e.g., pins and slots), one or more solenoids configured to engage/ disengage, multiple solenoids configured to engage/disengage, etc. Moreover, the additional joint can be configurable/"set" to any of variety of different positions and actuation behaviors. In other implementations, the actuation/repositioning of the additional joint is accomplished via software. Any joint described herein can include any combination of the functionalities set forth in this paragraph.

Figure 5:
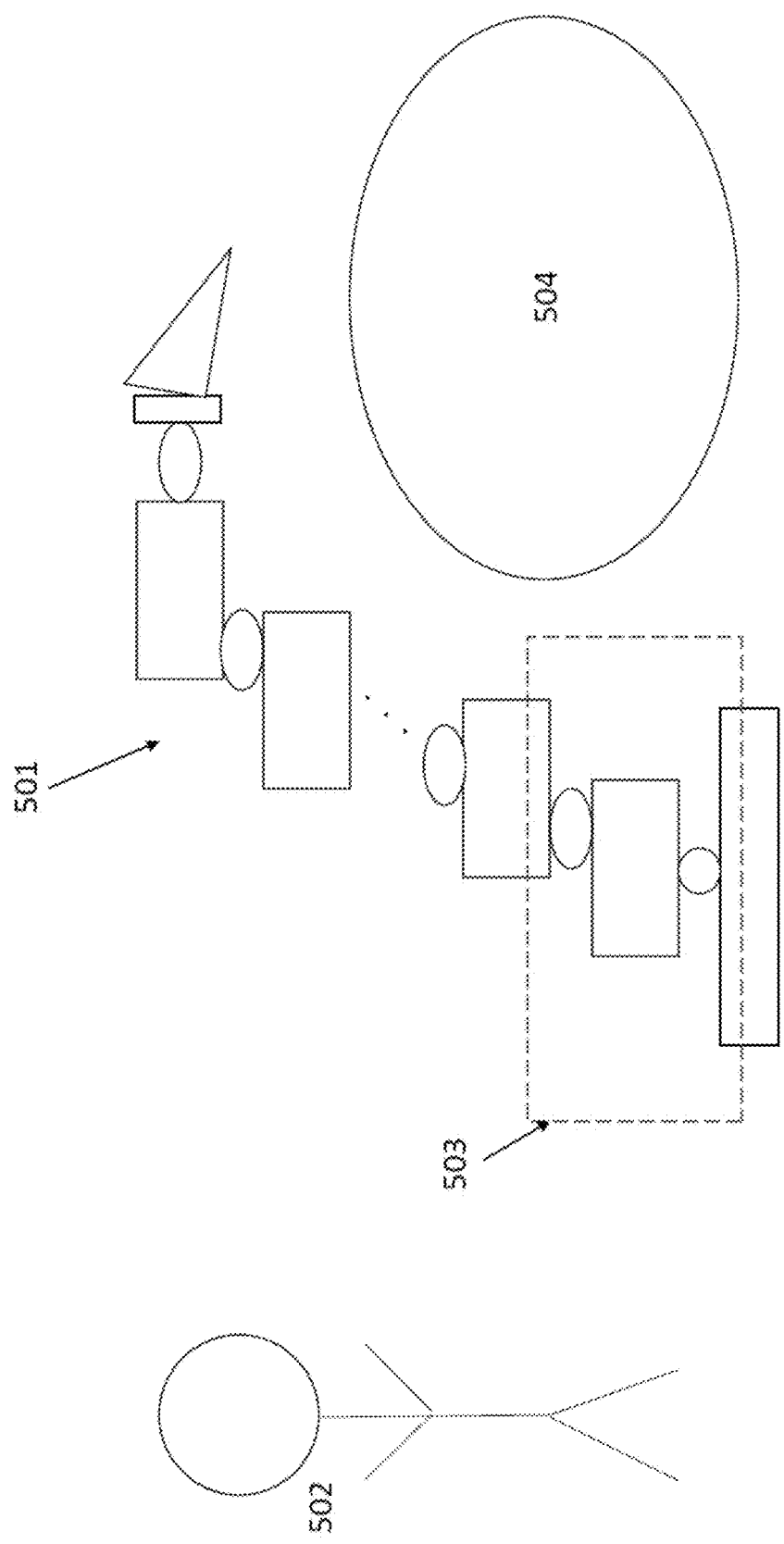
FIG. 5 shows a diagram of a robot and a cushion, according to an embodiment.

In some implementations, a safety device can be employed at and/or near a robot to protect an operator of the robot. For example, as shown in FIG. 5, to protect an operator 502 from the robot 501 acting in a non-normal way or acting under shutdown procedures, a safety device (in the form of a cushion 503) can be included in the environment of the robot 501. The robot 501 may have a normal performance area 504, but may sometimes depart from the normal performance area 504. In some implementations, the safety device is a cushion 503 that can either surround the base of the robot 501 or an upper portion of the robot 501. The cushion 503 can be made of a variety of materials, such as foam, feather, polyester, wool, leather, nylon, and/or the like. In some implementations, the cushion 503 can be an inflatable or partially inflatable cushion which deploys upon being triggered, for example in response to a power loss or malfunction of the robot 501 or other predefined event. For example, the cushion 503 can store air and inflates in a manner similar to that of compact air cushions used in motor vehicles when an impact is sensed. The cushion 503—whether already there to warn the operator 502 regarding work envelope area or whether inflated due to a sensed error—can prevent the operator 502 from getting unnecessarily close to the robot 501. The cushion 503 being inflatable effectively alerts the operator 502 of the sensed unexpected event, as well as provides a safe manner of contact.

In FIG. 6A, an example robot arm or manipulator is shown raised or tilted/angled back, together with its base attachment, according to an embodiment. In some implementations, a solenoid 601 is located in a portion of the base 602 of the robot 600 or other attachment location, so that when the electric current ceases, the effective magnet behavior of the solenoid 601 ceases, and the portion having the solenoid 601 as an attachment ceases to be attached (e.g., to a base attachment). For example, when the solenoid 601 ceases to act as an attachment method for the base 602 to the underlying support structure, the base 602 can lift up or disengage from another portion of the base 602 and/or a robot base attachment 603, allowing the robot arm or manipulator to move away from the entity 604 in a safe manner. In FIG. 6A, the solenoid 601 acts as an attachment method for a portion of the robot base attachment 603 to a support, table, standalone base, or moveable carriage. The solenoid 601 also can include a screwed hinge, spring attachment, or other attachment which allows the robot arm or manipulator to angle back or tilt or otherwise relocate away from the entity 604. In an embodiment, the robot base 602 tilts away from the support or other base.

Figure 6C:
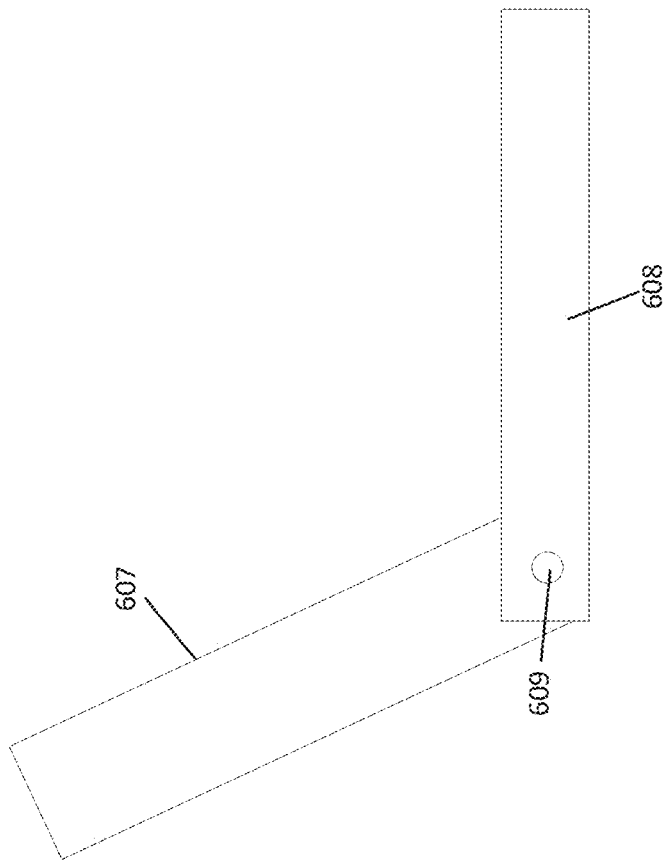
FIG. 6C shows a block diagram visualizing a robot arm after tilting/moving/angling away from the base, according to an embodiment.
Figure 6B:
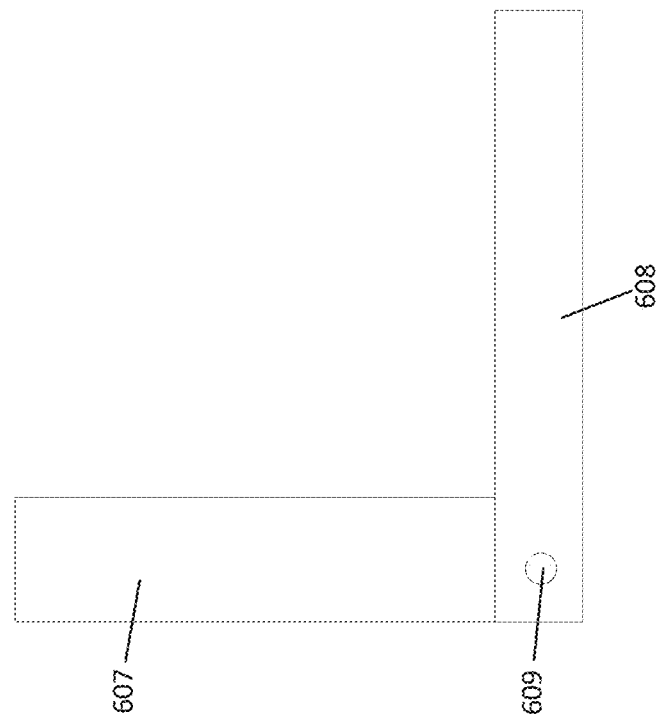
FIG. 6B shows a block diagram visualizing a robot arm before tilting/moving/angling away from a base, according to an embodiment.

FIG. 6B shows a block diagram visualizing a robot arm before tilting/moving/angling away from a base, according to an embodiment. FIG. 6B shows a robot arm 607, a base 608, and a joint 609 (e.g., including a solenoid) when the robot arm 607 has not tilted/moved/angled away from the base 608. FIG. 6B may represent a scenario in which the overall assembly (including the robot arm 607, the base 608, and the joint 609) is locked in place (e.g., by the solenoid or other locking/brake mechanism). The configuration of FIG. 6B can also represent a scenario in which a stop condition (e.g., a loss or deliberate removal of power) has not occurred. FIG. 6C shows a block diagram visualizing the robot arm of FIG. 6B after tilting/moving/angling away from the base, according to an embodiment. FIB. 6C shows the robot arm 607 tilted/moved/angled away from the base 608, pivoting at joint 609. FIG. 6C may represent a scenario in which a stop condition (e.g., loss or deliberate removal of power) has occurred, such that one or more components of the assembly can translate and/or rotate.

Figure 6D:
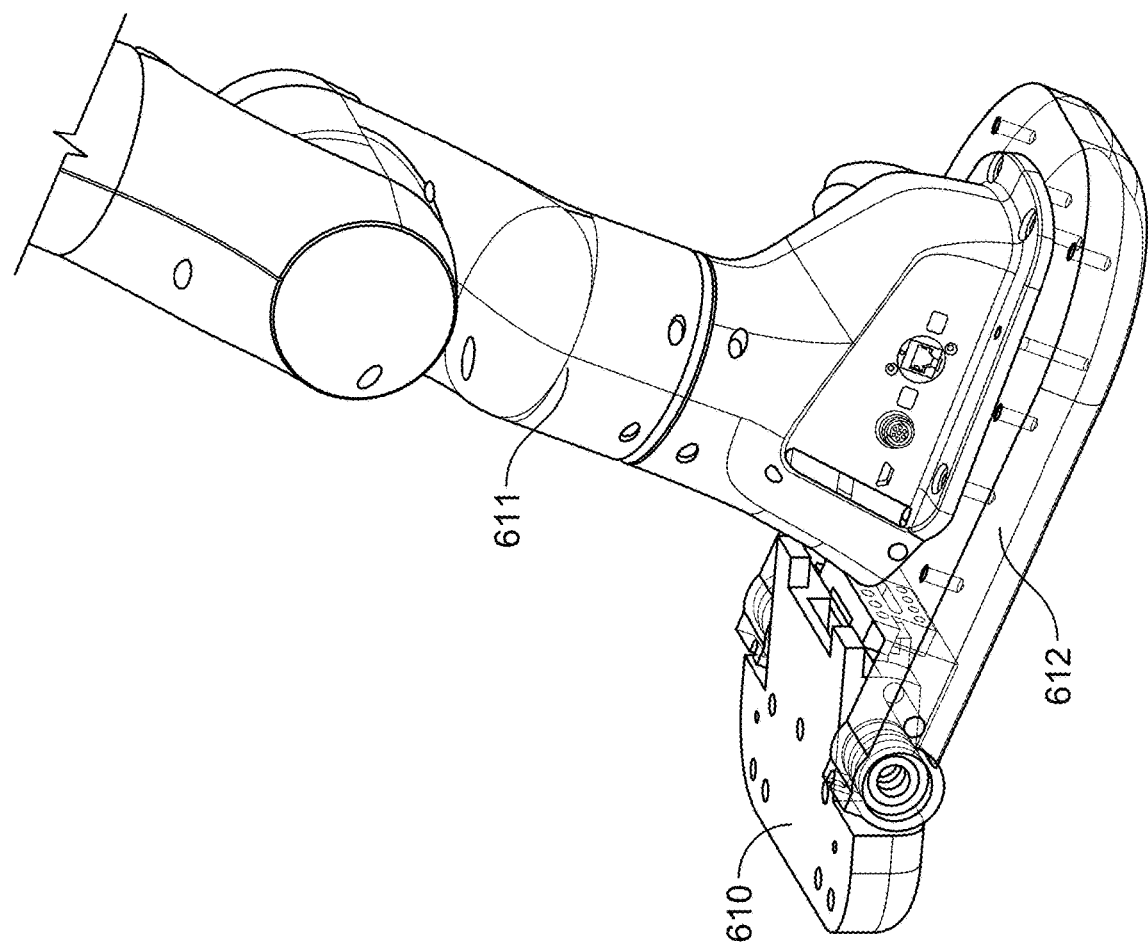
FIG. 6D shows a zoomed in image for a joint area that visualizes a robot arm tilting/moving/angling away from a base, according to an embodiment.
Figure 6E:
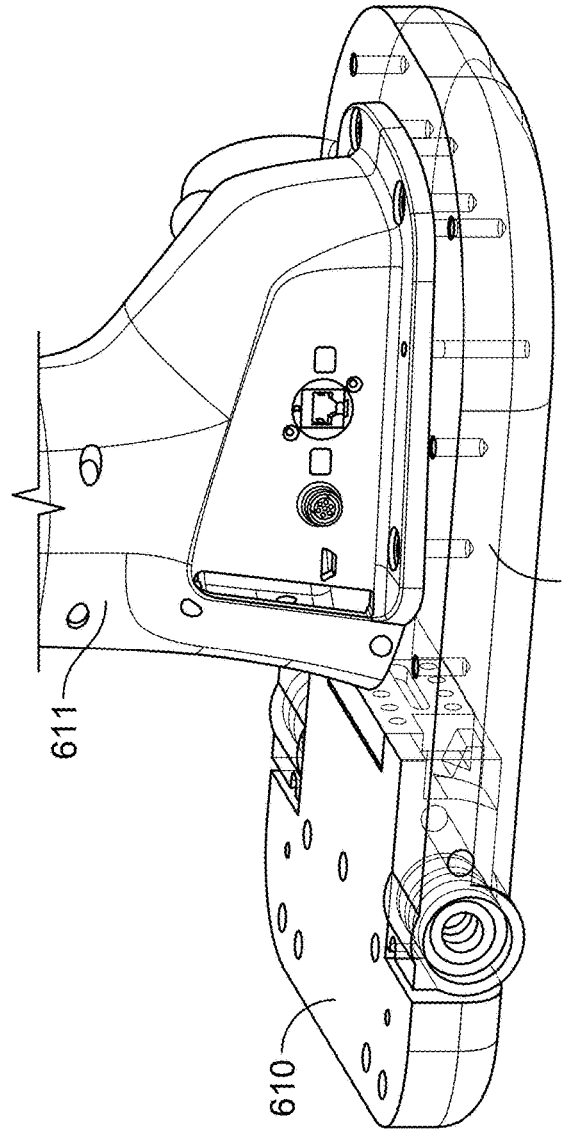
FIG. 6E show a zoomed in image for a joint area when the robot arm is not titled/moved/angled away from a base, according to an embodiment.
Figure 6F:
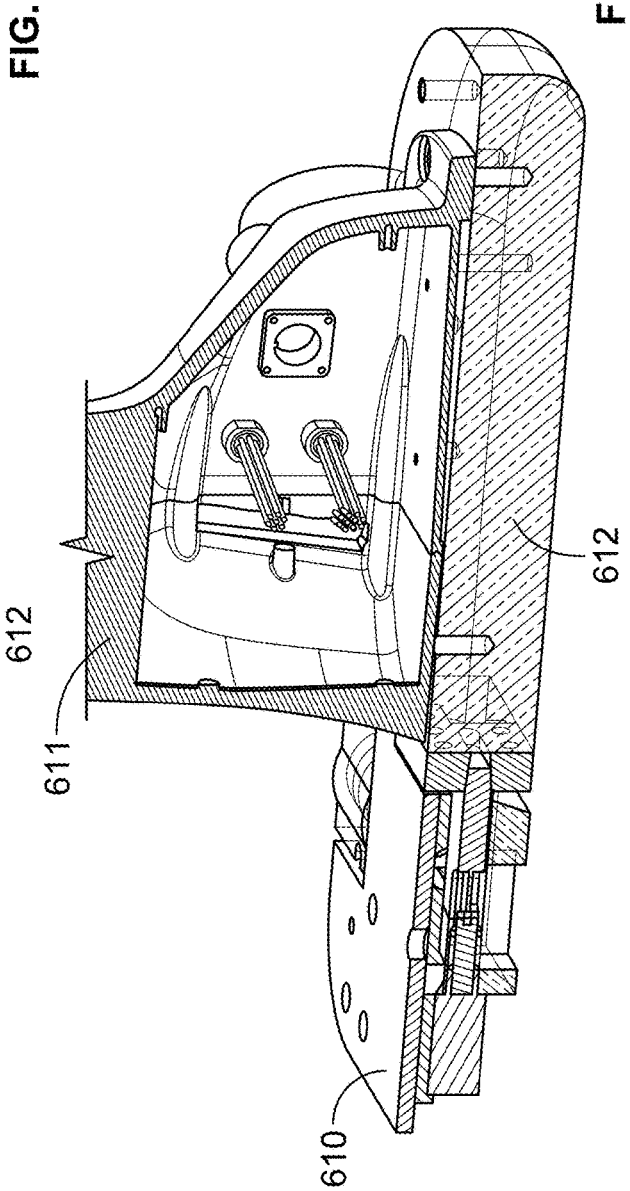
FIG. 6F show a zoomed in image for a joint area when the robot arm is not titled/moved/angled away from a base, according to an embodiment.

FIG. 6D depicts a joint region of a robot assembly, in which a robot arm is tilting/moving/angling away from a base, according to an embodiment. Component 610 is part of and/or attached to a base, while component 611 is part of and/or attached to a robot arm. When a stop condition is met, component 612 can move/tilt/rotate such that component 611 and/or the robot arm tilts/moves/angles away from component 610. For contrast, FIGS. 6E and 6F depict the joint region when the robot arm is not titled/moved/angled away from a base, according to an embodiment. As shown in FIG. 6D, component 612 in FIGS. 6E and 6F has not moved/titled/rotated away from component 610.

Figure 7:
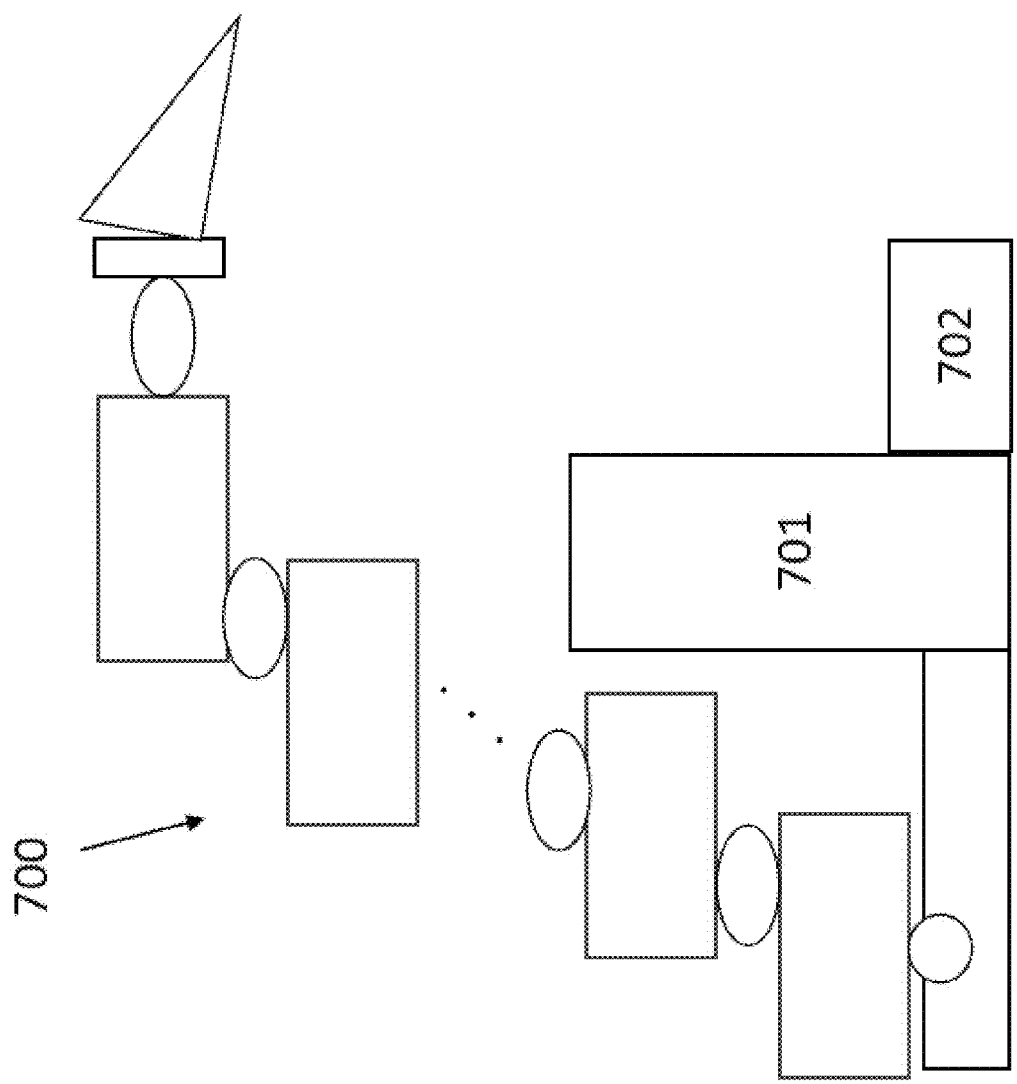
FIG. 7 shows a diagram of a robot with a barricade, according to an embodiment.

In FIG. 7, a limiting device 701 (e.g., mechanical barricade) can be used to prevent a robot 700 from causing additional undue harm in the event of an error or unexpected loss of power while working on an entity, while undergoing maintenance, undergoing cleaning, and/or the like. In some implementations, the limiting device 701 can restrict the maximum space by stopping or causing to stop all robot motion and is independent of the controller. In some implementations, the limiting device 701 is associated with a support structure 702 (e.g., blockage, wall, floor, gantry, ceiling) near the robot. The support structure 702 can assist with maintaining a position and/or orientation of the limiting device 701. In some implementations, the limiting device 701 can be made of metal, plastic, or any other hard material which is always present at the support structure—whether independent from the robot 700 or attached to the bottom portion of the robot 700. In some implementations, the limiting device 701 can be made of inflatable material, which inflates upon a sensed loss of power, error, or other event, and prevents the robot 700 from moving or falling completely on an entity.

In FIG. 8, an embodiment of a robot device 800 having a robot arm 805 acting upon an entity 801 is shown, where the entity 801 is lying down on a support structure 802 such as a table or other horizontal support structure. Actions of the robot arm 805 are controlled by a controller 803 operatively coupled to a memory 804, the controller 803 providing electronic instructions to the arm 805 of the robot device 800 to make contact, via an attached end effector 806, with the entity 801 and to effect/perform one or more actions. The one or more actions can include, e.g., a massage, a treatment of a specific area of the entity, and/or a resistance testing of a specific area of the entity. The entity 801 can be, for example, a person, an animal, a soft body, or an inanimate object. In this embodiment, an electronic shutdown is caused by the controller 803, the controller 803 receiving a command from a sensor or electronic device 807 measuring and/or providing data to the controller about the robot device 800 or the entity 801. In this embodiment, the entity 801 or another can effect an electronic shutdown of the robot device 800 via a remote control switch which connects to the controller 803 of the robot device 800. The remote control switch can be wired, Bluetooth® enabled, and/or a device software app soft switch enabled over LAN or WLAN network connection.

One or more embodiments provide for one or more disabling features of the robot, which can be used in conjunction with or triggered by an electronic shutdown of the robot. For example, a robot device is disabled by an entity or another manually with a safety mechanical switch or lever associated with at least one of the joints and/or joint brakes connecting and/or connected between the robot arm links. For example, the safety mechanical lever can be a lever piece which can be moved upward or downward, depending upon the type of system. The safety mechanical lever manually releases a brake on the respective joint to which it is attached. The brake on the joint is what locks the respective joint so that the robot is configured to maintain itself in a rigid manner upon error and/or loss of power and does not fall down onto the entity or damage the robot itself by hitting into another device.

In an embodiment, the brake on the respective joint is electromechanical and is controlled by at least one of: the controller commanding a locking or an unlocking of the joint brake and/or a use of a mechanical level or switch to physically disable the joint brake.

In an embodiment, if the robot is powered down either intentionally or unintentionally, at least one or more of the joints of the robot arm are not braked or locked. This can allow a person having the massage or a person nearby to manually move the robot arm away from the body to allow the person to depart safely from the treatment area. In an embodiment, a mechanical or electro-mechanical brake of the wrist of the robot is removed so that it cannot be enabled. In an embodiment, a mechanical or electro-mechanical $5^{th}$ brake (relative to the base) of a 6-axis robot is removed so that it cannot be enabled in the event of a loss of power. In an embodiment, a mechanical or electro-mechanical $6^{th}$ brake (relative to the base) of a 7-axis robot is removed so that it cannot be enabled in the event of a loss of power.

In an embodiment, an override of the at least one brake is effected by at least one of a safety-rated force sensor, contact sensor, or soft/hard button.

In the course of the interaction protocol, it may occur that the person becomes uncomfortable. In such case, a switch, button, or sensor can be used by the person or operator or automatically by a sensor acting on stored threshold data to interrupt the interaction protocol being effected.

In some implementations, the software-defined interface (e.g., tablet/device) or stop button is directly attached to the robot device to allow for switch off, and/or engagement or disengagement of brakes by application of or stopping of power via a portable power or other power source, depending upon the brake type employed at specific brake joints of the robot.

Some implementations can use additional safety features such as warning lights, audible alarm or music to alert or identify an error or change in situation. In some implementations, additional safeguarding techniques can be employed, including limiting devices, sensors, fixed barriers, and interlocked barrier guards, flashing lights, signs, whistles, and horns. For example, additional safeguarding techniques can be attached to the robot device and/or communicate with a controller associated with (e.g., included in) the robot device.

In an embodiment, the robot has at least one sensor on its outer surface—directed away from the entity being worked on by the robot—to detect when an operator or another is approaching and/or within the robot's working envelope, to effect a "slow" speed or restriction of movement. In an embodiment, the robot has at least one sensor on its outer surface—directed away from the entity being worked on by the robot—to detect when an operator or another is approaching and/or within the robot's working envelope, to trigger an inflation device surrounding the robot and preventing an operator from entering a critical working area of the robot, e.g., should the power cease unexpectedly or the robot experience a malfunction. In an embodiment, the at least one sensor includes a presence sensing device (e.g., camera, motion detector, etc.).

Embodiments can be used with each other in the same system in order to provide additional redundancy for a safer system.

As described herein, some robot arms/manipulators employ a braking system that can only be disabled electronically. For those robots using power-on electromagnetic brakes, such brakes are only or can only be "on" when the power is on. This means, that when the power is off, the brakes disengage and all joints loosen. This can cause damage to the robot, as well as any persons nearby, in the event of an unexpected power loss. A battery or capacitive storage associated with the robot joints can allow for a slow decrease of power, in the event of power loss from the main source. A cushion, as described herein, can be used to catch or soften the unexpected fall of the robot. For those robots using power-off electromagnetic brakes, such brakes are only or can only be "on" when the power is off. This means, that when the power is off, the brakes lock causing the robot to be immovable. The various embodiments regarding this type of brake is described above in, for example, FIGS. 1 and 2. Some robot arms/manipulators employ a braking system that can be manually released, and employ a manual release lever that allows a person to override the brake when there is no power. In some implementations, a manual release lever is added to at least the brakes located at the wrist joint, the second to last joint, or another joint, to allow for manual movement of the robot arm so that a person can depart safely, but also prevent the heavy robot arm from falling or partially falling on the person. The robot arm joints allow for not only lateral movement, but also vertical movement, which must be taken into account when adding a manual release brake to the robot arm.

Other brakes that can be employed are spring engaged brakes which lock when the power is off, and thus, can be manipulated in systems of at least some implementations as described herein. Permanent magnet brakes in the robot arm joints can allow for usable brakes when the system is on and off, since the magnetic field can continuously flow, and can force parts of the brake to engage in a frictional relationship with the joint, causing the brake to manually lock.

In embodiments, a portable power source could be a battery, such as a 24 volt battery or other size depending upon the robot type and size.

In an embodiment, the table (or work table or surface) under the body or object is able to articulate the different parts of the body independently. Throughout the specification, the surface or structure supporting the body or object is referred to as "table" for ease of reference in embodiments but is not meant to be limited to a table. The supporting structure or surface can be the ground, a chair or other furniture, a highly adjustable table, or other structure or means of support. The support structure can include a sensor, a button or other device which disables the robot device. The support structure can include a mechanical structure which allows an operator or body to physically move the robot away via a track that is unlocked. The support structure can include a mechanical safety block that resides there permanently or inflates or somehow appears during a detected error situation. In embodiments, a system, method, and apparatus provide for a therapeutic massage plan applied by a robot with one or more arms, to the body of a human lying prone, face down, on a massage table. The robot arm(s) can be positioned to the side of the table such that the workspace reach of each robot arm substantially covers the target regions of the therapeutic massage. In an embodiment, the mounting position of the robot arm(s) is determined to increase and/or maximize the pressure application required for the therapeutic massage. In embodiments, the therapeutic massage or other plan can be effected on the front region or a side or other region of a body. In embodiments, the therapeutic massage or other plan can be effected on a body which is human, mammal, animal, or a non-living object. In embodiments, the therapeutic massage or other plan can be effected on non-living soft body objects. Accordingly, it can be desirable in some instances to provide electromechanical safety features for protecting the entity receiving a massage, as described in various embodiments herein.

FIG. 9 shows a flowchart of a method 900, according to an embodiment. In some implementations, method 900 can be performed using an apparatus that includes a base (e.g., base 101, 201, or 602). The apparatus can further include a robotic arm (e.g., arm 102, 202, 402, or 805). The robotic arm can be operatively coupled to the base via a connector (e.g., connector 111 or 211). The robotic arm can include a set of links (e.g., links 103a-n, 203a-n, or 403a-n) interconnected by a set of joints (e.g., joints 104a-n, 204a-n, or 404a-n). A first link (e.g., link 103n, 203n, or 403n) from the set of links can be operatively coupled to the connector. Each joint from the set of joints can include a brake from a set of brakes. Each brake from the set of brakes can be enabled (e.g., locked, braked) or disabled (e.g., unlocked, not braked). The apparatus can further include an end effector (e.g., end effector 105, 205, 407, 806) operatively coupled to the robotic arm. For example, the end effector can be operatively coupled to the robotic arm via a second link (e.g., link 103a, 203a, 403a) from the set of links different from the first link. The end effector can be directly coupled to the second link, or coupled to the end effector via one or more intermediate components (e.g., device 112, sensor 106, device 212, sensor 206, manipulator 405, or wrist 406). The apparatus can further include a controller communicatively coupled to at least one of the base, the robotic arm, or the end effector. The controller can be configured to perform method 900. In some implementations, the apparatus can include a support structure that is configured to support an object associated with a task to be performed by the robotic arm. The support structure can be attached to the base. In some implementations, the apparatus can include a mechanical switch (e.g., button, lever, etc.) and/or a software-defined interface (e.g., tablet, phone, remote, etc.) operatively coupled to the base, the robotic arm, the end effector, and/or the controller.

At 901, the robotic arm is caused to perform a task. The task could be, for example, a massage, medical procedure, assembly, and/or the like. Causing the robotic arm to perform the task can include the controller sending an electronic signal representing the task to be performed to one or more components of the robotic arm. In some implementations, the task includes causing the end effector to make contact with and/or come in close contact (e.g., within 1 inch, within 6 inches, within 12 inches, etc.) with a person and/or a deformable body.

At 902, a determination is made, during the task, that movement of the robotic arm is to be restricted. Movement of the robotic arm being restricted can refer to, for example, restricting all or some movements of the robotic arm. Examples of situations that can cause the determination to be made can include, for example, low power, no power, reduction in power to below a predefined power threshold value, a selection by a user via a mechanical button, a selection by a user via an electronic device, a detected malfunction, a sensor reading outside an acceptable range, an undesirable environmental condition, an operator getting too close to the robotic arm (e.g., within 5 feet, within the normal working area of the robotic arm, etc.), and/or the like. In some implementation, the determination that movement of the robotic arm is to be restricted can be made based on a human using the mechanical switch and/or the software-defined interface to request that the movement of the robotic arm be restricted.

At 903, a first subset of brakes is enabled in response to determining that movement of the robotic arm is to be restricted. The first subset of brakes can be included in the set of brakes. Enabling the first subset of brakes can cause each brake in the first subset of brakes to be locked/braked. The first subset of brakes can include, for example, all brakes except the brake furthest from the base (i.e., the closest brake to the end effector) and/or the brake second furthest from the base (i.e., the second closest brake to the end effector). Alternatively, the first subset of brakes can include, for example, all brakes except the brake furthest from the base (i.e., the closest brake to the end effector), the brake second furthest from the base (i.e., the second closest brake to the end effector), and the brake third furthest from the base (i.e., the third closest brake to the end effector), for example to facilitate movement control in three directions (e.g., cartesian x, y, and z directions). In some implementations, 903 can happen automatically (e.g., without requiring human intervention) in response to 902. In some implementations, the first subset of brakes are enabled by receiving a signal sent from the controller.

At 904, a second subset of brakes are disabled in response to determining that movement of the robotic arm is to be restricted. The second subset of brakes are included in the set of brakes. The second subset of brakes are different than he first subset of brakes. Disabling the second subset of brakes can cause each brake in the second subset of brakes to be unlocked/not braked. The second subset of brakes can include, for example, the brake furthest from the base (i.e., closest brake to the end effector) and/or the brake second further from the base (i.e., second closest brake to the end effector). The second subset of brakes can include all brakes from the set of brakes that are not included in the first subset of brakes. In some implementations, the second subset of brakes are disabled by receiving a signal sent from the controller. In some implementations, 904 can happen automatically (e.g., without requiring human intervention) in response to 903. In some implementations, 904 and 903 can occur at substantially the same time (e.g., within 0.1 second of, within 0.5 second of, within 1 second of, within 2 second of, etc.).

In some implementations of method 900, the task includes causing the end effector to make contact with a person and/or a deformable body, and disabling the second sub of brakes facilitates movement of the end effector away from the person and/or the deformable body (e.g., by the person, the deformable body, by a different person, etc.).

In some implementations of method 900, the task includes causing the end effector to make contact with a person and/or a deformable body, and enabling the first subset of brakes and disabling the second subset of brakes: (1) minimizes an amount of unfixed rotational inertia associated with the robotic arm, (2) minimizes (or at least decreases) an amount of unsupported weight of the robotic arm on the person and/or the deformable body, and/or (3) minimizes (or at least decreases) an amount of force sufficient to break contact between the end effector and the person and/or the deformable body.

The apparatus performing method 900 is not limited to having one robotic arm (see, e.g., FIG. 4). The apparatus can include, for example, two or more robotics arms. Therefore, in some implementations of method 900, the base is a first base, the robotic arm is a first robotic arm, the connector is a first connector, the set of links is a first et of links, the set of joints is a first set of joints, the set of brakes is a first set of brakes, the end effector is a first end effector, and the task is a further task. The apparatus further includes a second base, which can be separate from or connected to the first base. The apparatus further includes a second robotic arm operatively coupled to the second base via a second connector. The second robotic arm can be separate from the first robotic arm. The second robotic arm can include a second set of links interconnected by a second set of joints. A first link from the second set of links can be operatively coupled to the second connector. Each joint from the second set of joints can include a brake from a second set of brakes. The second set of brakes can include a third subset of brakes and a fourth subset of brakes. Each brake from the second set of brakes can be configured to be enabled or disabled.

In an embodiment, an apparatus comprises a base (e.g., base 101, 201, or 602). The apparatus further comprises a robotic arm (e.g., arm 102, 202, 402, or 805) operatively coupled to the base via a connector (e.g., connector 111 or 211). The robotic arm includes a set of links (e.g., links 103a-n, 203a-n, or 403a-n) interconnected by a set of joints (e.g., joints 104a-n, 204a-n, 404a-n). A first link (e.g., link 103n, 203n, or 403n) from the set of links is operatively coupled to the connector. Each joint from the set of joints includes a brake from a set of brakes, each brake from the set of brakes configured to be enabled (e.g., locked, braked) or disabled (e.g., unlocked, not braked). The apparatus further comprises an end effector (e.g., end effector 105, 205, 407, or 806) operatively coupled to the robotic arm via a second link (e.g., link 103n, 203n, or 403n) from the set of links different from the first link. The end effector can be directly coupled to the second link, or coupled to the end effector via one or more intermediate components (e.g., device 112, sensor 106, device 212, sensor 206, manipulator 405, or wrist 406). The apparatus further comprises a controller, communicably coupled to at least one of the base, the robotic arm, or the end effector. The controller is configured to cause the robotic arm to perform a task, and determine, during the task, that movement of the robotic arm is to be restricted.

In some implementations, at least one brake from the set of brakes is freely removable by a human (e.g., human the task is being performed on, an operator, or any other human) such than an orientation or a position of the end effector is modifiable (e.g., human the task is being performed on, an operator, or any other human). For example, the human can remove the at least one brake and push and/or pull the robotic arm to modify the orientation and/or position of the robotic arm and/or the end effector.

In some implementations, the set of brakes include at least one friction brake, and an orientation and/or position of the robotic arm, when the set of brakes are enabled and/or disabled, (1) does not change due to gravity (e.g., stays in place without other external forces), and (2) does change due to force being provided by a human to the robotic arm.

In some implementations, the at least one brake from the set of brakes is configured to allow at least one joint form the set of joints to move in a first direction but not a second direction different than the first direction. For example, the second direction could be all other directions different than the first direction. The first direction can be linear and/or rotational.

In some implementations, the controller is further configured to send a signal to cause at least one brake from the set of brakes to be configured in one of a first mode or a second mode. In the first mode, the at least one brake is configured to allow at least one joint from the set of joints to move in a first direction but not a second direction different than the first direction. In the second mode, the at least one brake is configured to allow the at least one joint to move in the second direction but not the first direction. The first direction can be linear and/or rotational. The second direction can be linear or rotational.

In some implementations, the controller is further configured to cause generation of an alarm in response to determining that movement of the robotic arm is to be restricted. For example, the alarm could be audible and/or visual. The alarm can be generated at the base, the robotic arm, the end effector, a remote compute device, a local compute device, and/or the like.

Any number of joints can be included in the plurality of joints (e.g., 2, 3, 4, 5, 6, 7, 8, 9, 10, etc.). In some implementations, the plurality of joints includes at least six joints. In some implementations, the plurality of joints includes at least seven joints.

In some implementations, determining that movement of the robotic arm is to be restricted is based on a reduction in power (e.g., at the apparatus and/or the robotic arm) to below a predefined power threshold value. The apparatus can be configured to automatically reposition the base (e.g., without requiring human intervention) in response to the power being below the predefined power threshold value.

In some implementations, the task causes the end effector to make contact with a person and/or a deformable body, and at least one brake from the set of brakes, when disabled (e.g., mechanically and/or electronically), facilitates movement of the robotic arm away from the person and/or the deformable body. For example, the at least one brake, when disabled, allows the person or a different person nearby modify a position and/or orientation of the robotic arm away from the person and/or deformable body.

In an embodiment, a non-transitory, processor-readable medium storing code representing instructions executable by a processor. The code comprises code to cause the processor to cause a robot to perform a task that includes causing an end effector (e.g., end effector 105, 205, 407, or 806) included in the robot to contact an object. The robot includes a set of links (e.g., links 103a-n, 203a-n, or 403a-n) interconnected by a plurality of joints (joints 104a-n, 204a-n, or 404a-n). Each joint from the plurality of joints includes a brake from a plurality of brakes. Each brake from the plurality of brakes is configured to be enabled (e.g., locked, braked) or disabled (e.g., unlocked, not braked). The plurality of brakes include a first set of brakes and a second set of brakes. The end effector is coupled (e.g., directly or via one or more intervening device) to at least one of a link from the set of links or an attachment device coupled to the link from the set of links. The code further comprises code to cause the processor to determine, during the task, that movement of the robot is to be restricted. The code further comprises code to cause the processor to enable the first set of brakes in response to determining that movement of the robot is to be restricted. The code further comprises code to cause the processor to disable the second set of brakes in response to determining that movement of the robot is to be restricted.

In some implementations, the code to cause the processor to determine that movement of the robot is to be restricted includes code to cause the processor to determine that movement of the robot is to be restricted based on received sensor data associated with a safety condition. The sensor data could be collected by, for example, a camera, a pressure sensor, a distance sensor, a motion sensor, a power sensor, and/or the like. The safety condition could be, for example, power less than a threshold, distance less than a threshold, pressure greater than a threshold, and/or the like.

In some implementations, the object is a human and the code to cause the processor to determine that movement of the robot is to be restricted includes code to cause the processor to determine that movement of the robot is to be response in response to a selection from the human (e.g., via a switch, a button, a lever, a selection on a compute device, and/or the like). Features of the various embodiments of the above-identified system and method described herein can be modeled and/or effected and/or controlled by a general computer, special purpose computer, a processor, and a smart device having a processor. Embodiments of the method instructions can be stored on a computer-readable medium, the medium being virtual or hardware or portable or in the cloud/networked, having instructions thereon which are readable or can be made to be readable by a computer or processor so that the computer software instructions can be executed. The various embodiments described herein, and those equivalents thereto, can be used for a variety of nonanalogous objects, e.g., human body, animal body, soft body having deformable characteristics, a non-homogenous body having soft and hard features. The various embodiments described herein, and those equivalents thereto, can be used for massage applications, sensing applications, modeling applications, and others.

The modifications listed herein and other modifications can be made by those in the art without departing from the scope of the disclosure. Although subject matter has been described herein with reference to specific embodiments, the invention(s) is not limited to the above embodiments and the specific configurations shown in the drawings. For example, some components shown can be combined with each other as one embodiment, and/or a component can be divided into several subcomponents, and/or any other known or available component can be added. The processes are not limited to those shown in the examples. Those skilled in the art will appreciate that the invention(s) can be implemented in other ways without departing from the substantive features of the invention. For example, features and embodiments described above can be combined with and without each other. The present embodiments are therefore to be considered in all respects as illustrative and not restrictive. Other embodiments can be utilized and derived therefrom, such that structural and logical substitutions and changes can be made without departing from the scope of this disclosure. This Specification, therefore, is not to be taken in a limiting sense, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This disclosure is intended to cover any and all adaptations and/or variations of various embodiments. Combinations of the above embodiments, and other embodiments not specifically described herein, will be apparent to those of ordinary skill in the art upon reviewing the above description.

The invention claimed is:

1. An apparatus, comprising:
    a base;
    a robotic arm operatively coupled to the base via a connector, the robotic arm including a set of links interconnected by a set of joints, a first link from the set of links operatively coupled to the connector, each joint from the set of joints including a brake from a set of brakes, the set of brakes including a first subset of brakes and a second subset of brakes, each brake from the set of brakes configured to be enabled or disabled;
    an end effector operatively coupled to the robotic arm via a second link from the set of links different from the first link, wherein at least one brake from the set of brakes is freely removable by a human such that an orientation or a position of the end effector is modifiable; and
    a controller, communicably coupled to at least one of the base, the robotic arm, or the end effector, the controller configured to:
        cause the robotic arm to perform a task;
        determine, during the task, that movement of the robotic arm is to be restricted;
        enable the first subset of brakes in response to determining that movement of the robotic arm is to be restricted; and
        disable the second subset of brakes in response to determining that movement of the robotic arm is to be restricted.

2. The apparatus of claim 1, wherein the task includes causing the end effector to make contact with a deformable body, and disabling the second subset of brakes facilitates movement of the end effector away from the deformable body.

3. The apparatus of claim 1, wherein the task includes causing the end effector to make contact with a deformable body, and enabling the first subset of brakes and disabling the second subset of brakes at least one of: (1) minimizes an amount of unfixed rotational inertia associated with the robotic arm, (2) minimizes an amount of unsupported weight of the robotic arm on the deformable body, or (3) minimizes an amount of force sufficient to break contact between the end effector and the deformable body.

4. The apparatus of claim 1, wherein the task includes causing the end effector to make contact with a deformable body.

5. The apparatus of claim 1, wherein determining that movement of the robotic arm is to be restricted is based on a reduction in power to below a predefined power threshold value.

6. The apparatus of claim 1, further comprising:
    a support structure configured to support an object associated with the task, the base being attached to the support structure.

7. The apparatus of claim 1, further comprising:
    at least one of a mechanical switch or a software-defined interface operatively coupled to at least one of the base, the robotic arm, the end effector, or the controller, the controller configured to determine that the movement of the robotic arm is to be restricted based on use of the at least one of the mechanical switch or the software-defined interface to request that the movement of the robotic arm be restricted.

8. The apparatus of claim 1, wherein the second subset of brakes includes at least one of a first brake located closer to the end effector than all remaining brakes from the set of brakes, a second brake located closer to the end effector than all remaining brakes from the set of brakes besides the first brake, or a third brake located closer to the end effector than all remaining brakes from the set of brakes besides the first brake and the second brake, the first subset of brakes including all brakes from the set of brakes not included in the second subset of brakes.

9. The apparatus of claim 1, wherein the base is a first base, the robotic arm is a first robotic arm, the connector is a first connector, the set of links is a first set of links, the set of joints is a first set of joints, the set of brakes is a first set of brakes, the end effector is a first end effector, and the task is a first task, the apparatus further comprising:
a second base;
a second robotic arm operatively coupled to the second base via a second connector, the second robotic arm including a second set of links interconnected by a second set of joints, a first link from the second set of links operatively coupled to the second connector, each joint from the second set of joints including a brake from a second set of brakes, the second set of brakes including a third subset of brakes and a fourth subset of brakes, each brake from the second set of brakes configured to be enabled or disabled; and
a second end effector operatively coupled to the second robotic arm via a second link from the second set of links different from the first link from the second set of links,
the controller, communicably coupled to at least one of the second base, the second robotic arm, or the second end effector, configured to:
cause the second robotic arm to perform a second task;
determine, during the second task, that movement of the second robotic arm is to be restricted;
enable the third subset of brakes in response to determining that movement of the second robotic arm is to be restricted; and
disable the fourth subset of brakes in response determining that movement of the second robotic arm is to be restricted.

10. An apparatus, comprising:
a base;
a robotic arm operatively coupled to the base via a connector, the robotic arm including a set of links interconnected by a set of joints, a first link from the set of links operatively coupled to the connector, each joint from the set of joints including a brake from a set of brakes, each brake from the set of brakes configured to be enabled or disabled;
an end effector operatively coupled to the robotic arm via a second link from the set of links different from the first link, wherein at least one brake from the set of brakes is freely removable by a human such that an orientation or a position of the end effector is modifiable; and
a controller, communicably coupled to at least one of the base, the robotic arm, or the end effector, the controller configured to:
cause the robotic arm to perform a task; and
determine, during the task, that movement of the robotic arm is to be restricted.

11. The apparatus of claim 10, wherein the set of brakes include at least one friction brake such that the orientation of the robotic arm, when the set of brakes are enabled, (1) does not change due to gravity, and (2) does change due to force being provided to the robotic arm.

12. The apparatus of claim 10, wherein at least one brake from the set of brakes is configured to allow at least one joint from the set of joints to move in a first direction but not a second direction different than the first direction.

13. The apparatus of claim 10, wherein the controller is further configured to:
send a signal to cause at least one brake from the set of brakes to be configured in one of a first mode or a second mode, the at least one brake configured to allow at least one joint from the set of joints to move in a first direction but not a second direction different than the first direction in the first mode, and the at least one brake configured to allow the at least one joint to move in the second direction but not the first direction in the second mode.

14. The apparatus of claim 10, wherein the controller is further configured to:
cause generation of an alarm in response to determining that movement of the robotic arm is to be restricted.

15. The apparatus of claim 10, wherein the set of joints includes at least six joints.

16. The apparatus of claim 10, wherein determining that movement of the robotic arm is to be restricted is based on a reduction in power to below a predefined power threshold value, and the apparatus is configured to automatically reposition at least one of the base or the robotic arm, without requiring human intervention, in response to the power being below the predefined power threshold value.

17. The apparatus of claim 16, wherein the apparatus is configured to automatically reposition the at least one of the base or the robotic arm, by at least one of:
translating the base along a direction extending away from a deformable body;
rotating the base away from the deformable body;
reducing a force applied to the deformable body by the robotic arm;
removing a force applied to the deformable body by the robotic arm; or
causing the end effector to cease making contact with the deformable body.

18. The apparatus of claim 10, wherein at least one of the base or the robotic arm includes a reconfigurable ratchet to selectively limit a first direction of movement of the at least one of the base or the robotic arm, and to facilitate incremental movement of the at least one of the base or the robotic arm in a second direction opposite the first direction.

19. The apparatus of claim 10, wherein:
the task causes the end effector to make contact with a deformable body, and
at least one brake from the set of brakes, when disabled, facilitates movement of the robotic arm away from the deformable body.

20. A non-transitory, processor-readable medium storing code representing instructions executable by a processor, the code comprising code to cause the processor to:
cause a robot to perform a task that includes causing an end effector included in the robot to contact an object, the robot including a set of links interconnected by a plurality of joints, each joint from the plurality of joints including a brake from a plurality of brakes, each brake from the plurality of brakes configured to be enabled or disabled, the plurality of brakes including a first set of brakes and a second set of brakes, wherein at least one brake from the plurality of brakes is freely removable by a human such that an orientation or a position of the end effector is modifiable, the end effector coupled to at least one of a link from the set of links or an attachment device coupled to the link from the set of links;

determine, during the task, that movement of the robot is to be restricted;

enable the first set of brakes in response to determining that movement of the robot is to be restricted; and disable the second set of brakes in response to determining that movement of the robot is to be restricted.

21. The non-transitory processor-readable medium of claim 20, wherein the code to cause the processor to determine that movement of the robot is to be restricted includes code to cause the processor to determine that movement of the robot is to be restricted based on received sensor data associated with a safety condition.

22. The non-transitory processor-readable medium of claim 20, wherein the code to cause the processor to determine that movement of the robot is to be restricted includes code to cause the processor to determine that movement of the robot is to be restricted in response to a user selection.

* * * * *